(12) United States Patent
Dimitrelos et al.

(10) Patent No.: US 10,688,410 B2
(45) Date of Patent: Jun. 23, 2020

(54) SYSTEMS AND METHODS OF CANNABIS OIL EXTRACTION

(71) Applicant: Evello International, LLC, Fort Lauderdale, FL (US)

(72) Inventors: Geronimos Dimitrelos, Plantation, FL (US); Bruce Vanaman, Fort Lauderdale, FL (US)

(73) Assignee: Evello International, LLC, Fort Lauderdale, FL (US)

(*) Notice: Subject to any disclaimer, the term of this patent is extended or adjusted under 35 U.S.C. 154(b) by 0 days.

(21) Appl. No.: 16/598,805

(22) Filed: Oct. 10, 2019

(65) Prior Publication Data

US 2020/0054962 A1    Feb. 20, 2020

Related U.S. Application Data

(63) Continuation-in-part of application No. 16/104,611, filed on Aug. 17, 2018, now Pat. No. 10,570,350.

(51) Int. Cl.
| | |
|---|---|
| *B01D 11/02* | (2006.01) |
| *B01D 1/08* | (2006.01) |
| *B01D 5/00* | (2006.01) |
| *B01D 19/00* | (2006.01) |
| *C11B 1/10* | (2006.01) |
| *A61K 36/185* | (2006.01) |

(52) U.S. Cl.
CPC ........ *B01D 11/0203* (2013.01); *A61K 36/185* (2013.01); *B01D 1/08* (2013.01); *B01D 5/006* (2013.01); *B01D 19/00* (2013.01); *C11B 1/104* (2013.01); *A61K 2236/15* (2013.01); *A61K 2236/333* (2013.01); *A61K 2236/37* (2013.01); *A61K 2236/39* (2013.01); *A61K 2236/53* (2013.01)

(58) Field of Classification Search
CPC ...... B01D 11/0203; B01D 1/08; B01D 5/006; B01D 19/00; A61K 36/185; C11B 1/104
See application file for complete search history.

(56) References Cited

U.S. PATENT DOCUMENTS

| | | | |
|---|---|---|---|
| 4,257,945 A | 3/1981 | Martel | |
| 7,259,231 B2 * | 8/2007 | Cornish | B01D 11/0203 209/133 |
| 7,622,104 B2 | 11/2009 | Whittle et al. | |
| 9,707,567 B2 * | 7/2017 | Bates | D01B 9/00 |
| 9,937,218 B2 | 4/2018 | Towle | |
| 10,155,176 B1 * | 12/2018 | Feuer | B01D 11/048 |
| 10,159,908 B2 | 12/2018 | Thomas | |
| 2004/0147767 A1 | 7/2004 | Whittle et al. | |

(Continued)

FOREIGN PATENT DOCUMENTS

| | | |
|---|---|---|
| CN | 106831353 A | 6/2017 |
| CN | 107898826 A | 4/2018 |
| WO | 2017184642 A1 | 10/2017 |

OTHER PUBLICATIONS

International Search Report and Written Opinion dated Oct. 2, 2019 of corresponding PCT Application No. PCT/US2019/40114.

*Primary Examiner* — Jonathan Miller
(74) *Attorney, Agent, or Firm* — Akerman LLP

(57) ABSTRACT

A cannabis oil extraction method includes performing grinding assisted extraction in the presence of solvent, co-solvent extraction with subcritical $CO_2$ comprising, degassing the $CO_2$ and separating the mixture by centrifugation.

21 Claims, 14 Drawing Sheets

(56) References Cited

U.S. PATENT DOCUMENTS

| | | |
|---|---|---|
| 2006/0106183 A1* | 5/2006 | Cornish ............ B01D 11/0203 528/1 |
| 2008/0128260 A1 | 6/2008 | Balass |
| 2013/0079531 A1 | 3/2013 | Barringer |
| 2016/0228787 A1 | 8/2016 | Payack |
| 2016/0287652 A1 | 10/2016 | Scott |
| 2016/0324908 A1* | 11/2016 | Bates ....................... D01B 9/00 |
| 2016/0346339 A1 | 12/2016 | Finley et al. |
| 2017/0020944 A1 | 1/2017 | Towle |
| 2017/0095518 A1 | 4/2017 | Bjorncrantz |
| 2017/0157529 A1* | 6/2017 | Chess ................ B01D 11/0203 |
| 2018/0000857 A1 | 1/2018 | Kotra et al. |
| 2018/0010066 A1 | 1/2018 | Stantchev |
| 2018/0078874 A1 | 3/2018 | Thomas |
| 2018/0147247 A1 | 5/2018 | Ivanov |
| 2018/0162828 A1* | 6/2018 | Nadal Roura ..... B01D 11/0492 |
| 2018/0214790 A1 | 8/2018 | Tucker |
| 2018/0296617 A1 | 10/2018 | Rivas |
| 2019/0099695 A1 | 4/2019 | Ko et al. |
| 2019/0099696 A1 | 4/2019 | Ko et al. |
| 2019/0143246 A1 | 5/2019 | Ko |
| 2019/0232190 A1 | 8/2019 | Rivas |

\* cited by examiner

1100

```
┌─────────────────────────────────────┐
│ Grinding assisted extraction in solvent │
│              1102                    │
└─────────────────────────────────────┘
                  ↓
      ┌───────────────────────┐
      │  Co-solvent extraction │
      │          1104          │
      └───────────────────────┘
                  ↓
      ┌───────────────────────┐
      │     Centrifugation     │
      │          1106          │
      └───────────────────────┘
                  ↓
      ┌───────────────────────┐
      │   Solvent Separation   │
      │          1108          │
      └───────────────────────┘
```

FIG. 14

SYSTEMS AND METHODS OF CANNABIS OIL EXTRACTION

CROSS-REFERENCE TO RELATED APPLICATIONS

This application is a continuation-in-part of U.S. patent application Ser. No. 16/104,611, filed Aug. 17, 2018. U.S. patent application Ser. No. 16/104,611 is hereby incorporated herein by reference.

TECHNOLOGY

The present disclosure is related to extraction techniques and systems for extracting cannabis oil from cannabis plants.

BACKGROUND

The cannabis plant include constituents such as cannabinoids having numerous therapeutically beneficial applications that have been used to treat a variety of diseases and conditions for centuries. For example, cannabinoids may be used to treat glaucoma, arthritis, insufficient appetite associated with anorexia or HIV/AIDS, posttraumatic stress disorder, insomnia, nausea arising from chemotherapy, and chronic pain, among others.

Among the medically significant cannabinoids found in the cannabis plant are tetrahydrocannabinol (THC), cannabidiol (CBD), and cannabidivarin (CBDV). In particular, THC has anti-inflammatory, analgesic, neuroprotective, and anticonvulsant properties. CBD has been found to have analgesic, anti-inflammatory, antispasmodic, and antipsychotic properties. Both CBD and CBDV are reported to have anticonvulsant properties useful in treatment of various forms of epilepsy, especially in children.

These cannabinoids, along with others, as well as terpenes and flavonoids may be extracted from the cannabis plant to harness their medicinal properties. The extracted oil may be further refined to isolate particular cannabinoids or blends of cannabinoids for desired uses.

Extracting cannabis oil from cannabis plants may generally employ a solvent or non-solvent based extraction technique. Non-solvent based techniques include rosin and dry sifting. Water-based techniques are also considered to be non-solvent based techniques. Solvent-based techniques for extracting cannabis oil include supercritical CO2 and hydrocarbon extraction.

Supercritical CO2 extraction utilizes high pressures and extremely low temperatures to extract cannabis oil using carbon dioxide in liquid form. While the CO2 may ultimately be removed from the final product, equipment cost is notably high and lacks scalability. Supercritical CO2 extraction is currently the preferred standard technique utilized by the industry.

Hydrocarbon extraction typically requires washing milled plant material with a liquid hydrocarbon solvent such as butane or propane. An alcohol may also be used. The mixture is then filtered and the filtrate is heated under vacuum to remove the solvent to produce butane hash oil. Winterization using an ethanol solvent may be used to clean the product and produce shatter.

SUMMARY

In one aspect, a cannabis oil extraction method comprises performing grinding assisted extraction, co-solvent extraction, degassing the $CO_2$, and separating the mixture by centrifugation. Grinding assisted extraction may include grinding plant material in the presence of solvent and performing co-solvent extraction using subcritical $CO_2$. Co-solvent extraction may include adding liquid $CO_2$ to the mixture. The mixture may be maintained at a temperature and pressure combination sufficient to maintain the liquid $CO_2$ in a subcritical state.

In one example, the plant material ground in the presence of the solvent is wet plant material.

In an above or a further example, a ratio of solvent to plant material present during the grinding assisted extraction is greater than 1:1 on a weight basis.

In an above or a further example, a ratio of solvent to plant material present during the grinding assisted extraction is greater than 2:1 on a weight basis.

In an above or a further example, grinding the plant material in the presence of solvent comprises grinding the plant material to micron scale. The plant material may be ground to less than 20 microns during grinding assisted extraction.

In an above or a further example, the solvent includes a food grade solvent. In an above or another example, the solvent is a non-polar solvent. The non-polar solvent may be selected from pentane, hexane, benzene, toluene, carbon tetrachloride, benzene, glycerol monooleate, diethyl ether, hexane, methylene chloride, carbon dioxide, methane, ethylene, D-limonene, olive oil, soybean oil, coconut oil, medium chain triglycerides, methanol, ethanol, propylene glycol, polysorbates 20 and 80 (tween 20 and 80), poloxamer 188, chloroform, diethyl ether, deuterated chloroform, or combination thereof. In one example, the solvent is glycerol monooleate.

In an above or a further example, the liquid $CO_2$ is added to the plant material and solvent mixture at ratio of greater than approximately 1:1 co-solvent to mixture on a weight basis.

In an above or a further example, the mixture is at a temperature between 30° C. and −18° C. and a pressure of between approximately 5.2 bar and approximately 72 bar when the liquid $CO_2$ is added to the mixture.

In an above or a further example, the method also includes agitating the mixture during co-solvent extraction with the liquid $CO_2$.

In an above or a further example, centrifugation separates the mixture into a solid phase, oil phase, and water phase. In one example, the oil phase comprises extract extracted from the plant and the method further comprises winterizing the extract in an inline winterization unit; filtering the winterized extract with a micron filter; preheating the filtered extract with a preheater; evaporating a first portion of the extract in an evaporation chamber of a short-path distillation unit, wherein a second portion of the extract passes through the evaporation chamber without evaporating; condensing the first portion of the extract in a vertical condenser; and evaporating one or more additional portions of the second portion of the extract in the same or one or more additional evaporation chambers at higher temperatures and condensing these one or more portions separately in the same or one or more additional vertical condensers to obtain refined cannabis oil pay product comprising cannabinoids isolated by weight.

In an above or a further example, degassing the $CO_2$ comprises heating the mixture before or during centrifugation.

In an above or a further example, at least a portion of the $CO_2$ is degassed during centrifugation.

In an above or a further example, degassing the $CO_2$ comprises allowing a supernatant component of the separated mixture generated by the centrifugation to expand.

In an above or a further example, heating the mixture after the co-solvent extraction to drive degassing of the liquid $CO_2$ co-solvent. Heating the mixture after the co-solvent extraction may include heating the mixture to between 26° C. and 32° C.

In an above or a further example, the method further includes collecting the $CO_2$ co-solvent degassed from the mixture.

BRIEF DESCRIPTION OF THE DRAWINGS

The novel features of the described embodiments are set forth with particularity in the appended claims. The described embodiments, however, both as to organization and manner of operation, may be best understood by reference to the following description, taken in conjunction with the accompanying drawings in which:

FIG. 14 is an extraction method according to various embodiments described herein.

DESCRIPTION

Figure 1:
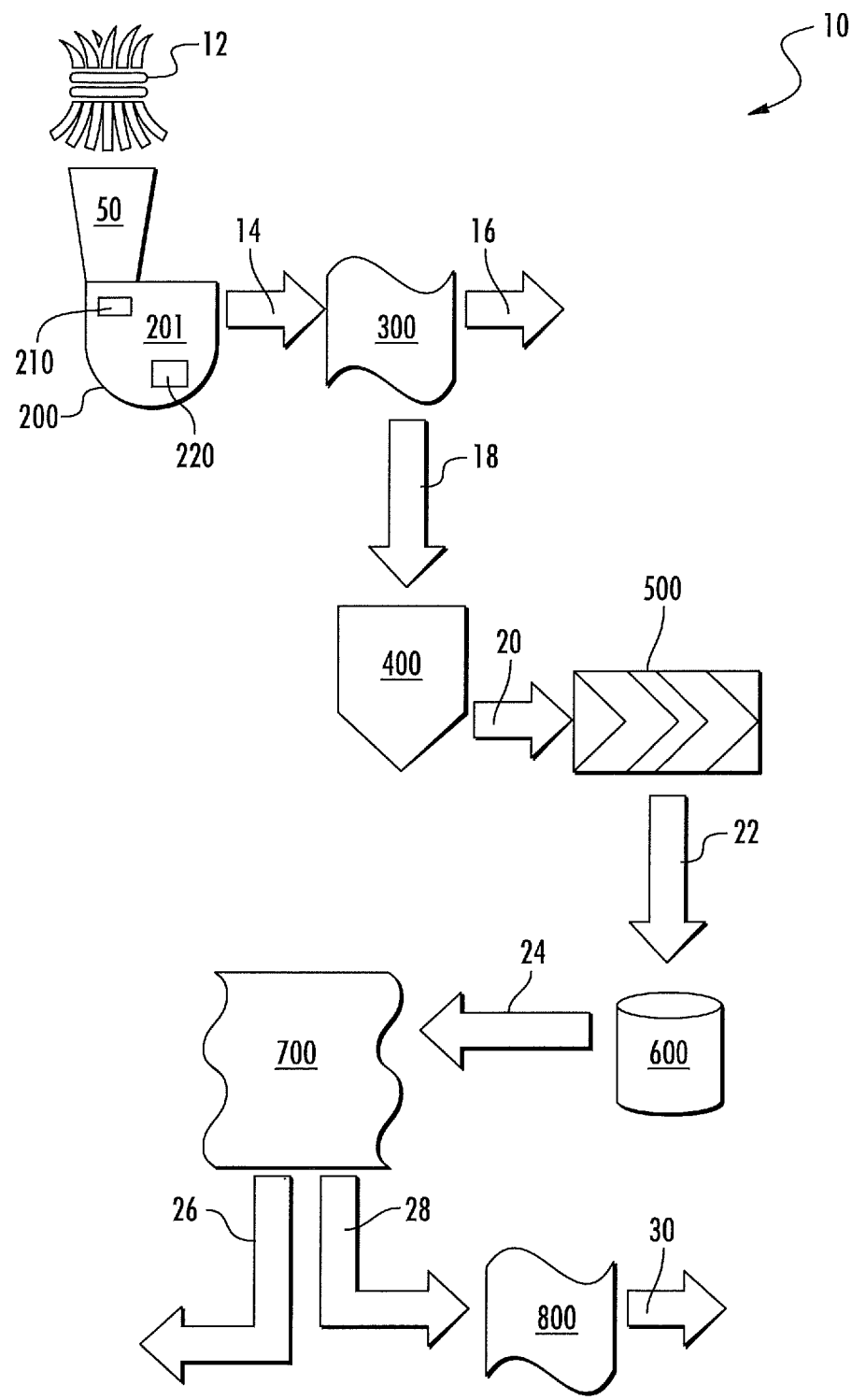
FIG. 1 is a schematic diagram of an extraction system according to various embodiments described herein.

The present disclosure describes an extraction system and method for extraction of cannabis oil from the cannabis plant *Cannabis sativa*. The method may include using the system to extract cannabinoids, e.g., tetrahydrocannabinol (THC), cannabidiol, and more than one hundred other cannabinoids, flavonoids, e.g., cannaflavins, terpenes, and terpenoids. The method may further include using the system to obtain refined oil extract products of one or more cannabinoids, one or more flavonoids, one or more terpenes, one or more terpenoids, or a combination thereof.

Current apparatus used to obtain cannabis oil do not include end-to-end processing. Furthermore, current apparatuses and methods are not scalable. For example, using supercritical $CO_2$ extraction on large-scale hemp operations cannot not be done in a cost effective manner and cannot refine the product or isolate cannabinoids.

In various embodiments, the extraction system includes an apparatus configured for the complete end-to-end processing of plants to extract cannabis oil and obtain a refined oil extract product. In one example, the extraction system may be configured for complete end-to-end processing of plants to obtain refined oil extract product including cannabinoids isolated at their weights and in custom concentrations to meet client needs.

In addition to not providing end-to-end processing or scalability, current high throughput extraction of cannabis oil does not utilize wet plant input. According to various embodiments herein, the extraction system may accept wet plant input and may not require that plants be dried prior to being fed into the system. Thus, embodiments of the extraction system disclosed herein may utilize plant input, e.g., straight from the fields; thereby avoiding time and costs associated with drying processes. Additionally, the extraction system may be operated proximate to the fields in which the plants grow to avoid transportation costs associated with transporting raw plant material to drying facilities or extraction systems.

FIGS. 1-13 illustrate various features and components of the extraction system 10 according to various embodiments wherein like numbers identify similar features and components.

The extraction system 10 may include various extraction components for performing various sub-processes of the extraction system 10 such as agitating, extracting, separating, heating, cooling, condensing, distilling, and/or refining products. Extraction components may also include components such as pumps for controlling pressure within the extraction system 10 or its sub-process equipment. In various embodiments, sub-process equipment may include one or more of an extraction unit 201 comprising an extraction vessel 200, condenser unit 301 comprising one or more condensers, winterization unit 400, filter unit 500, preheater 600, short-path distillation unit 700, or condenser unit 801 (see, e.g., FIG. 1).

In some embodiments, the extraction system 10 may include or be in fluid communication with storage vessels for storage of product, including intermediate or refined pay materials, processing material such as solvent, and/or thermal medium such as oil, water, or other fluid.

The extraction system 10 may also include transport components such as one or more of transport lines 14, 16, 18, 20, 22, 24, 26, 28, 30 (FIG. 1) for transporting product and/or processing materials between sub-process equipment. Transport lines may generally comprise a flow path through which fluid may be transported. For example, transport lines may include piping or plumbing. Transport components may also include thermal transport lines for transporting thermal mediums to one or more sub-process equipment and/or transport lines 14, 16, 18, 20, 22, 24, 26, 28, 30. Transport components may also include apparatus for controlling transport of product, processing material, and/or thermal medium such as valves and pumps.

The extraction system 10 may also include thermal components such as heaters, coolers/refrigerators, and/or insulated liners or jacketing for providing precise temperature control during processing, which in some embodiments may include during transport of product and/or processing materials between sub-process equipment and/or storage vessels. In some embodiments, one or more thermal components may be associated with a sub-process equipment or transport component. For example, one or more sub-process vessels, transport lines 14, 16, 18, 20, 22, 24, 26, 28, 30, storage vessels, or combinations thereof may be jacketed for circulation of a thermal medium. Thermal components may also include storage vessels for storage of thermal mediums. In one example, transport components such as thermal medium pumps and thermal medium transport lines may be used to transport thermal mediums between heaters or coolers configured to impart desired thermal state to thermal mediums and one or more processing apparatus, transport lines 14, 16, 18, 20, 22, 24, 26, 28, 30, thermal medium storage vessels, or combination thereof.

With particular reference to FIG. 1, illustrating a schematic diagram of the extraction system 10 according to various embodiments, plant material 12, which may also be referred to as feed, may be fed into an extraction vessel 200 for extraction of crude extract. The rate and volume of feed fed into the extraction vessel may depend on the application. Considerations may include choice of solvent; solvent depth or volume relative to plant material; vessel pressure; temperature; plant material, piece size, or density; agitation rate or mechanical energy input; or sound transducer parameters, as examples.

In some embodiments, the extraction system 10 includes a transport component comprising a feed delivery subsystem 50. The feed delivery subsystem 50 may include, for example, one or more of a pipe, hopper, chute, belt, auger, or combinations thereof along which plant material 12 may be transported and/or delivered into the extraction vessel 200. In some embodiments, the amount of plant material fed into the extraction vessel 200 may be metered by the feed delivery system 50 to control the amount of feed subject to extraction. For example, the feed delivery system 50 may include a feed belt wherein the speed of the feed belt may be modified to control feed supply. In this or another example, an opening into the extraction vessel 200 may be selectively opened, closed, or restricted to control feed supply. In a further example, the feed delivery system may include feed containers or partitions that hold discrete amounts of plant material that may be delivered into the extraction vessel 200 in a controlled sequence. In one example, the feed is fed into the extraction vessel 200 at a continuous rate.

Figure 12:
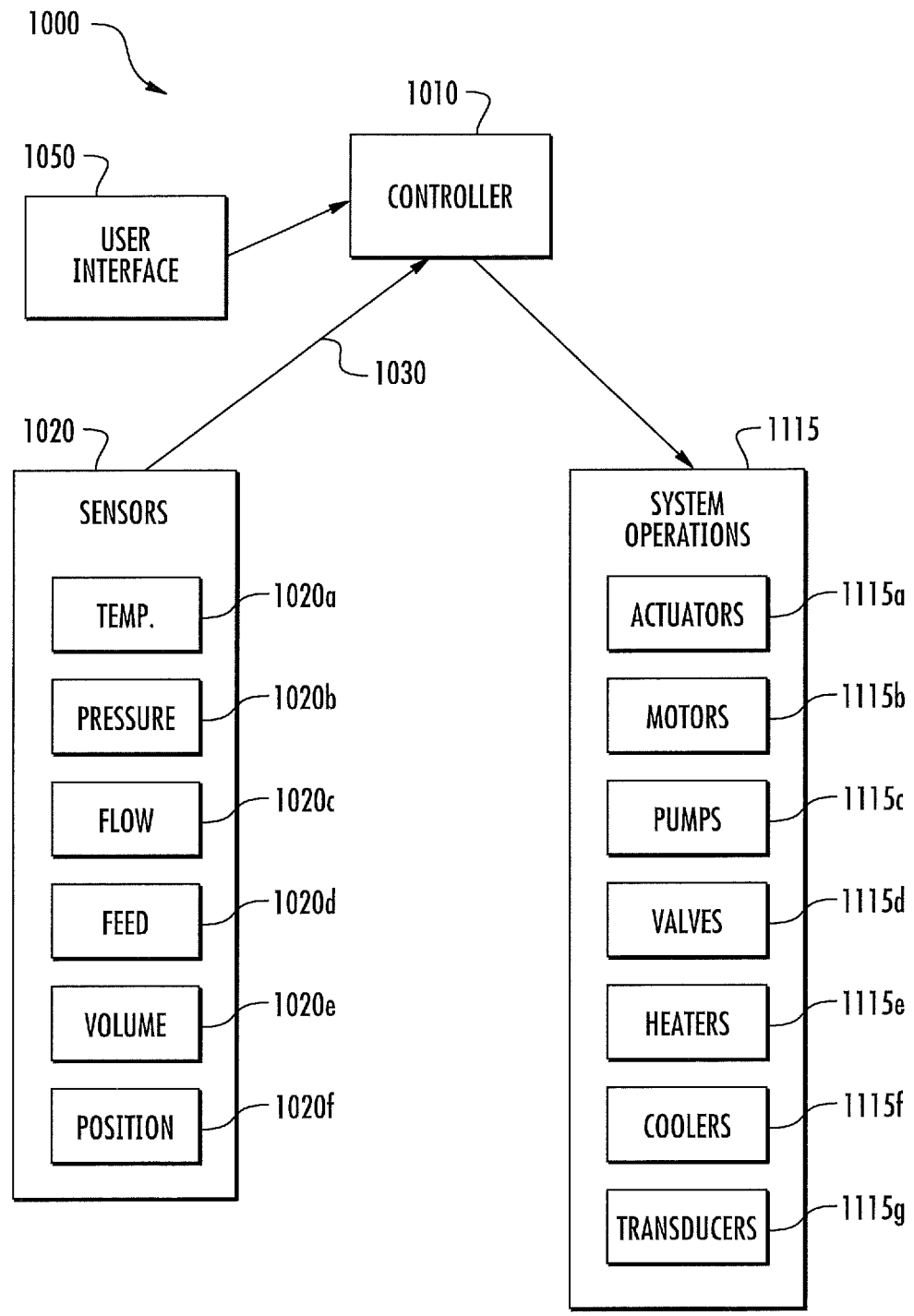
FIG. 12 is a schematic of a control system of the extraction system according to various embodiments described herein.
Figure 13:
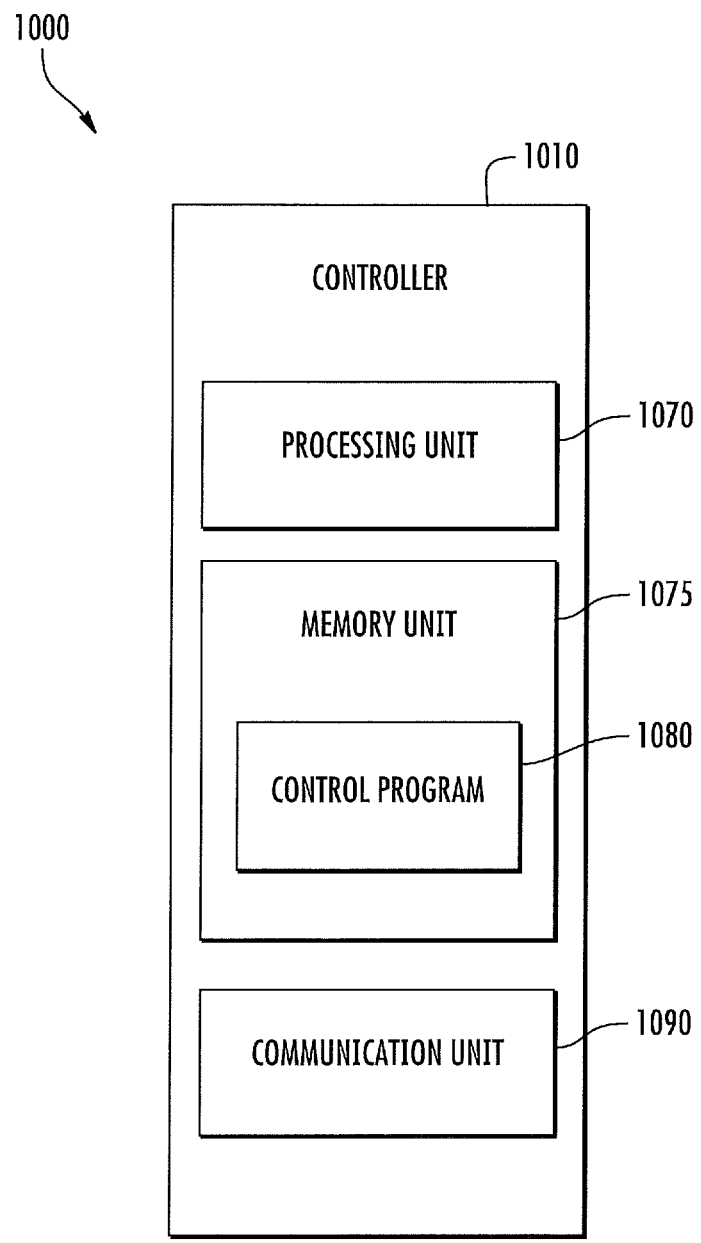
FIG. 13 is a further schematic of the control system including hardware units according to various embodiments described herein.

In any of the above or another example, and with further reference to FIGS. 12 & 13, the extraction system 10 may include a control system 1000. The control system 1000 may include a controller 1010 operable to system operations 1015, e.g., processes and parameters, of the control system 1000. In one embodiment, the controller 1010 may be operable to control parameters such a temperature of product, processing materials, or environment with respect to one or more sub-process equipment, transport lines 14, 16, 18, 20, 22, 24, 26, 28, 30, or combinations thereof. For example, the controller 1010 may be operable to actuate valves to control flow or pressure, initiate or adjust operations of pumps, heaters, coolers, agitators, or other system operations 1015.

In various embodiments, the control system 1000 may include or communicate with one or more sensors 1020 to obtain extraction process data 1030 from which the controller 1010 analyzes to determine various control operations. The extraction process data 1030 may be transmitted from the one or more sensors 1020 to the controller 1010 via wired or wireless communication port. For example, the communication port, which may include multiple communication ports each associated with one or more sensors 1020 may include a transmitter or transceiver to transmit the extraction process data 1030 to communication port 1040, which may include or communicate with a receiver or transceiver to receive the transmitted extraction process data 1030. In some embodiments, the one or more sensors 1020 include thermal sensors, pressure sensors, optical sensors, video or image sensors, proximity sensors, flow sensors, proximity sensors, motion sensors, moisture sensors, weight sensors, sound or electromagnetic wave sensors (transmitter, receiver, or transceivers), capacitance sensors, or other sensors.

In one embodiment, the controller 1010 may receive extraction process data 1030 comprising temperature data from one or more temperature sensors 1020*a* positioned to measure temperature of product, processing material, or environment with respect to one or more sub-process equipment, transport lines 14, 16, 18, 20, 22, 24, 26, 28, 30, or combinations thereof. The controller 1010 may analyze the temperature data and modify system operations 1015 as necessary to maintain or obtain a desired temperature. For example, the controller 1010 may adjust flow rates of thermal medium and/or increase or decrease heater or cooler outputs with respect to processing apparatus, transport lines 14, 16, 18, 20, 22, 24, 26, 28, 30, thermal medium, or combinations thereof.

In one embodiment, the controller 1010 may receive extraction process data 1030 comprising pressure data from one or more pressure sensors 1020*b* positioned to measure pressure associated with one or more sub-process equipment, transport lines 14, 16, 18, 20, 22, 24, 26, 28, 30, or combinations thereof. The controller 1010 may analyze the pressure data and modify system operations 1015 as necessary to maintain or obtain a desired pressure. For example, the controller 1010 may initiate an evacuation pump to increase or decrease pressure or may open or close a flow or pressure relief valve. The control system 1000 may also be configured to react to warning and/or shutdown events. For example, the controller 1010 may initiate a warning such as a sound, light, indication on a user display panel, or a notification message sent by email, text, or other messaging protocol, for example, if pressure data indicates a threshold deviation from a programed parameter. In some embodiments, the controller 1010 may be programed to shut down one or more sub-process equipment if pressure data indicates a threshold deviation from a programed parameter. In one example, the controller 1010 may be configured to shutdown processing via the extraction unit 201 or extraction vessel 200 thereof when pressure data indicates pressure is above approximately −10 psi. When configured for initiating a warning and shutdowns, the threshold for a shutdown event may represent a greater deviation than that for a warning event.

In one embodiment, the controller 1010 may receive extraction process data 1030 comprising temperature data from one or more temperature sensors 1020*b* positioned to measure temperature associated with one or more sub-process equipment, transport lines 14, 16, 18, 20, 22, 24, 26, 28, 30, or combinations thereof. The controller 1010 may analyze the temperature data and modify system operations 1015 as necessary to maintain or obtain a desired temperature. For example, the controller 1010 may initiate increase power to heaters or coolers or an increase in flow to one or more sub-process equipment, transport lines 14, 16, 18, 20, 22, 24, 26, 28, 30, or combinations thereof to increase or decrease a processing environment temperature. The control system 1000 may also be configured to react to warning and/or shutdown events. For example, the controller 1010 may initiate a warning such as a sound, light, indication on a user display panel, or a notification message sent by email, text, or other messaging protocol, for example, if temperature data indicates a threshold deviation from a programed parameter. In some embodiments, the controller 1010 may be programmed to shut down one or more sub-process equipment if temperature data indicates a threshold deviation from a programed parameter. When configured for initiating a warning and shutdowns, the threshold for a shutdown event may represent a greater deviation that for a warning event.

In one embodiment, the controller 1010 may receive extraction process data 1030 comprising flow rate data from one or more flow sensors 1020c positioned to measure flow associated with one or more sub-process equipment, transport lines 14, 16, 18, 20, 22, 24, 26, 28, 30, thermal transport lines, or combinations thereof. The controller 1010 may analyze the flow data and modify system operations 1015 as necessary to maintain or obtain a desired flow. For example, the controller 1010 may initiate a pump to increase or decrease flow rate.

In one embodiment, the control system 1000 may receive extraction process data 1030 comprising feed data from one or more feed sensors 1020d positioned to measure plant material 12 or input rate of plant material 12. In some embodiments, the one or more feed sensors 1020d include optical sensors, video or imaging, weight sensors, sound or electromagnetic wave sensors (transmitter, receiver, or transceivers), capacitance sensors, or other sensors positioned to collect corresponding feed data to be utilized by the controller 1010. The controller 1010 may utilize the feed data to control the amount of plant material 12 delivered into the extraction vessel 200. For example, the controller 1010 may modulate system operations 1015, such as belt speed, flow, opening or closing of a chute or opening into the extraction vessel 200 or a holding area, or augur speed, for example, to control feed rate. In some embodiments, a use may utilize the user may interface 1050 to identify, measure, or specify the plant material feed rate.

The control system 1000 may include a user interface 1050 to interface a user with the control operations of the control system 1000. The user interface 1050 may be used to select predefined processes that may include predefined parameters of one or more components or processing apparatuses. In some embodiments, the user interface 1050 may be used to individually address parameters of one or more processing apparatus, extraction component, transport component, thermal component, or combination thereof to define or modify an associated operation or parameter of the extraction system. In one embodiment, the control system 1000 includes a database 1060 for storing processing protocols defining operations of the extraction system 10. For example, the database 1060 may include a plurality of processing protocols that may be selected by a user, e.g., via the user interface 1050, to control specific operations of the extraction system 10. In a further example, the plurality of processing protocols includes specification of cannabinoid weights or weight ranges to be output from refining processing.

In one embodiment, the database 1060 further include algorithms for conforming operations and associated processing parameters to feed characteristics. For example, the database 1060 may include algorithms for adjusting feed rate, solvent amount, flow rates, pressure, temperature, or other parameters with respect to an input or measure amount of plant material fed into the extraction system 10. In a further example, the user interface 1050 allows a user to select one or more of a plurality of processing protocols and an amount of plant material input. The controller 1010 may utilize the protocol and algorithms to modify and scale operations and associated processing parameters accordingly to achieve the desired output. As described in more detail below, processing protocols may include solvent selection according to desired extraction product and/or transducer frequency parameters. Similarly, a user may utilize the user interface 1050 to select solvent or solvent blends, agitation rate, extraction duration, and/or transducer frequency parameters and/or durations.

With continued reference to FIG. 1, as noted above the plant material 12 may be wet; however, plant material 12 may also be delivered into the extraction vessel 200 dry. In various embodiments, the plant material 12 is preferably preprocessed into pieces having a largest dimension of approximately 1 to 2 inches (+/−10%) or less. The plant material may be cut or ground. Other size pieces may be used, such as larger pieces having a largest dimension less than 5 inches or less than 3 inches or smaller pieces having a largest dimension less than 1 inch or less than half an inch, for example. Larger pieces may also be used but may reduce yield and/or increase extraction time and overall process efficiency. A thresher or grinder may be used, for example. Beneficially, hammer-milling is not required, although hammer-milling could be used. For optimal efficiency and product quality hammer-milling may not be recommended as hammer-milling may result in product degradation. As described in more detail below, the extraction system 10 may be equipped with extraction components such as agitators configured to work the plant feed in a manner and environment less detrimental to the cannabis oil components that are the target of the extraction.

In some embodiments, the extraction system 10 may include or be configured to operate in conjunction with a preprocessing subsystem comprising a grinding apparatus (not shown). The preprocessing system may be in-line with the extraction vessel 200 or delivery system 50 to grind plants 12 prior to the ground pieces being fed into the extraction vessel 200. For example, a mechanical cutter or grinder may preprocess plant material and the ground plant material may then be transported, which may be metered, as described above, into the extraction vessel 200 via the delivery subsystem 50. In one embodiment, the delivery system 50 includes an integrated preprocessing system comprising a grinder. In various embodiments including a control system 1000 (FIGS. 12 & 13), the control system 1000 may also utilize the one or more sensors 1020, such as feed sensor 1020d, to monitor plant piece sizes. For example, when the feed data indicates a piece size larger or smaller than desired the controller 1010 may stop delivery of plant material 12, generate a notification, e.g., an audio alarm, or adjust cutting or grinding operations to obtain the desired piece size or range of piece size.

The extraction vessel 200 may define an interior volume into which the plant material 12 may be subjected to the cannabis oil extraction process. The interior volume may also be configured to receive an extraction solvent, which may be multiple solvents or co-solvents. According to one method, the extraction system 10 utilizes an extraction solvent comprising one or more food grade solvents, such as food grade ethanol. The solvents may include a blend of solvents or food grade solvents. As a result of the extraction, the cannabis oil including cannabinoids, terpenes, and flavonoids may be extracted from the plant material 12 and taken up within solvent to form a solvent/extraction mixture.

As described in more detail below, the solvent/extraction mixture may then be evaporated into gas and steam for subsequent separation.

In various embodiments, the extraction unit 201 may include one or more extraction components comprising an agitator. The agitator may be configured to disrupt or agitate the mixture of solvent and plant material 12 within the interior volume of the extraction vessel 200. For example, the extraction unit 201 may include a mechanical agitator 210 that positions within the interior volume of the extraction vessel 200. The mechanical agitator 210 may include one or more agitation members that may translate or rotate vertically, horizontally, or at another angle within the interior volume. The one or more agitation members may include extensions configured to engage plant material 12 and/or solvent to move the plant material 12 and/or within the interior volume to thereby agitate the mixture. In various embodiments, a mechanical agitator 210 may be mounted in the center of the interior volume of the extraction vessel 200 to move the plant material 12 evenly through the duration of the oil extraction from the plant material 12. In one embodiment, the mechanical agitator 210 may be driven by a motor connected to the agitation member, e.g., the agitation member may include a shaft that the motor rotates. In some embodiments, the mechanical agitator 210 is driven by a moving magnetic field, which may be generated by a magnetic field generator or by a motor output driving a magnet or magnetic attractive material.

In any of the above or another embodiment, the extraction unit 201 may include a sonic agitator. For example, the extraction unit 201 may include a transducer 220 comprising one or more sonic or ultrasonic transducers. The transducer 220 may be configured to generate vibrations or soundwaves within the solvent held within the interior volume of the extraction vessel 200. For example, the transducer 220 may be implemented for sonication at amplitudes adapted for cellular disruption of the plant material 12 to assist in breaking up the plant material 12 and bonds. The transducer 220 may be a full spectrum transducer for producing full spectrum soundwaves. In some embodiments, the transducer 220 may generate soundwaves between 5 kHz and 250 kHz or more. In one example, the transducer 220 may rotate through frequencies to provide full spectrum emission through the solvent to target a wide spectrum of plant material densities. Amplitude may be held constant or varied. In one example, the transducer 220 may rotate through multiple frequency blocks.

In embodiments including a control system 1000 (FIGS. 12 & 13), the controller 1010 may be configured to monitor and/or control solvent supply, e.g., modulate pumps and valves, transducer 220, e.g., sonic wave forms or parameters, and/or mechanical agitator 210. For example, the control system 1000 may operatively couple to the transducer 220 and/or mechanical agitator 210, e.g., to device specific controllers or power delivery to transducer 220 or motor for driving agitator member, to selectively control the associated operations of the transducer 220 and/or mechanical agitator 210. The controller 1010 may also be used to specify particular solvent blends. It has been found that different plant materials require different solvents and different lengths of extraction time for optimal extraction and that different soundwave frequencies for disrupting bonds of organic material and oil (pay material) have correspondence to density of the pay material (oil) extracted. For example, rotating frequencies at different densities of plant material with different solvents produces different effects with respect to extraction of particular cannabinoids. In various embodiments, the transducer 220 may be operated at specific frequencies or frequency ranges to target specific cannabinoids. The transducer 220 may also be operated at multiple specific frequencies or frequency ranges to target multiple cannabinoids. The transducer 220 may include multiple transducers positioned to emit soundwaves into the interior volume of the extraction vessel 200. In some embodiments, the multiple transducers may comprise an array of transducers. The array of transducers may include one or more radial arrays of transducers positioned about a perimeter of the interior volume to direct soundwaves toward a center or other portion of the interior volume. In various embodiments, the transducer 220, or one or more transducers thereof, may be movably mounted to control a direction of soundwave emission. For example, the transducer 220, or one or more transducers thereof, may be pivoted in vertical, lateral, or other directions. In one example, the controller 1010 may be configured to operate a positioning motor or actuator to direct the transducer 220, or one or more transducers thereof. In a further example, the controller 1010 may direct the transducer 220, or one or more transducers thereof, in multiple directions during an extraction process. For example, the controller 1010 may direct the transducer in a first direction for a first period of time and in a second direction for a second period of time.

Various frequencies and combinations of frequencies, including rotating frequencies may be used. As introduced above, the extraction system 10 may include a control system 1000. In one embodiment, a user may enter information via the user interface 1050 related to the plant material subject to extraction. The information may relate to the density of the plant material and/or other information such as plant type, quality, water content, or other information related to the plant material. In one example, one or more sensors 1022 are used to determine plant density, e.g., optical sensor, electromagnetic wave or field transmitter and receiver, weight sensor, or capacitance sensor, or other plant information to be used to select extraction parameters. In various embodiments, the controller 1010 may increase a programed residence time based on measured or entered parameters, e.g., via the user interface 1050. For example, plant material with higher oil content may correspond to shorter residence time with respect to initial oil extraction with the extraction vessel 200. The controller 1010 may use this information to determine extraction parameters such as frequency, mechanical agitation rate, solvent volume, or residence time in the extraction vessel 200. For example, the control system 1000 may include a control program 1080 for determining the extraction parameters or extraction protocol corresponding to the plant information received. In one example, an extraction protocol specifies a residence time of approximately 1 to 4 hours. Plant material that is more fibrous, denser, dryer, and/or longer, e.g., compared to a set standard or numerically specified by an extraction protocol or program of the control program 1080, may result in the controller 1010 utilizing a longer residence time or selecting an extraction protocol or program having a longer residence time, while less fibrous, less dense, wetter, and/or shorter plant material may result in the controller 1010 initiating a shorter residence time. The control program 1080 may also include a plurality of extraction programs for controlling the system operations 1015 according to the extraction parameters determined by the controller 1010. The extraction programs may comprise instructions that when executed by the controller 1010 control system operations 1015 according to a defined sequence and method. Various measured or entered parameters with respect to the plant material and/or target extraction components may specify particular extraction programs specifying a particular extraction protocol for controlling the extraction system operations 1015. In some embodiments, the controller 1010 or instructions of an extraction program are configured to respond to feedback provided by sensors during the extraction process to modify the extraction program based on measured conditions or input by a user.

In various embodiments, the extraction vessel 200 may further be heated. For example, the extraction unit 201 may include or the extraction vessel 200 may be associated with a thermal component such as a heater positioned to heat the interior volume. In one example, the extraction vessel 200 comprises a thermal component comprising a jacket. The jacket may jacket the extraction vessel 200 or interior volume thereof and include an interior volume that a thermal medium may be flowed within to transfer heat to the interior volume of the extraction vessel 200. The thermal medium may include a heated fluid such as hot gas, water, steam, or oil, for example. In one embodiment, the solvent may also be warmed prior to mixing with the plant material 12.

In some embodiments, the extraction unit 201 may include an extraction component comprising a vacuum pump or otherwise be configured for evacuation of the extraction vessel 200 to near vacuum, e.g., from between approximately 10 psi to approximately −15 psi, such as between approximately 5 psi to approximately −10 psi. The vacuum pump may be fluidically coupled to the interior volume of the extraction vessel 200 and operable to evacuate atmosphere and reduce pressure within the interior volume.

Thus, in one embodiment, plant material 12 may be delivered into an extraction vessel 200 and mixed with solvent. The mixture may be mechanically agitated with an agitation member and disrupted by sonication. The cannabis oil may be extracted from the plant material 12 and be contained within a solvent/extract mixture. The interior volume may be heated and evacuated to near vacuum prior to, during, or following extraction. The extract includes cannabinoids, terpenes, and other materials.

A low-pressure environment within the interior volume of the extraction vessel 200 assists in vaporization by decreasing boiling points of the mixture constituents. Consequently, lower heat or energy input is required to drive vaporization of the solvent/extraction mixture. The lower temperatures required for evaporation also lowers cannabinoid burn off and degradation.

The solvent/extraction mixture may exit the extraction vessel 200 in gas and steam. Thus, the extraction vessel 200 may further comprise a vaporization vessel. However, in other embodiments, the solvent/extraction mixture may be transported from the interior volume utilized for extraction to one or more separate vaporization vessels comprising separate or distinct interior volumes for vaporization. In some such embodiments, one or more of these vaporization vessels may be at near vacuum and may be heated as described above and elsewhere herein with respect to the extraction vessel 200. In some embodiments, the extraction unit 201 or extraction vessel 200 thereof includes a series of extraction vessels 200. The extraction vessels 200 may be provided in parallel, for example, and feed the condenser unit 301, which may include a single condenser 300 or multiple condensers 300.

Embodiments including a control system 1000 (FIGS. 12 & 13), may include a controller 1010 configured to monitor and/or control transducer duration and frequency, plant material resident time within the extraction vessel, duration of agitation, plant material and associate processing materials such as solvent volume, and/or temperature. The extraction vessel 200 and associated extraction process may therefore be scalable with respect densities and types of cannabis oil extraction processes. The extraction system 10 may therefore be variable in temperature, density, duration, frequency range. The extraction process with respect to the extraction vessel 200 may utilize a temperature controlled vessel and variable frequency transducers to produce a variety of extracted products to provide customization of the extraction process.

The extraction system 10 may also be scalable in capacity. For example, multiple sub-process equipment may be provided in series or parallel. Multiple storage tanks may also be coupled together to collect.

The extraction system 10 may be configured for batch or continuous processing. For example, remaining biomass may be removed from the extraction vessel 200, e.g., through a bottom discharge port, upon completion of the extraction. Additional plant material and solvent may then be introduced into the interior volume of the extraction vessel 200 for subsequent extraction.

Transport component 14 may be configured to transport the gas and steam solvent/extraction mixture from the extraction vessel 200 to the condenser unit 301. Transport component 14 may comprise one or more flow paths fluidically coupled to the extraction vessel 200 and condenser unit 301, for example.

As introduced above, the condenser may be evacuated to a pressure lower than atmosphere, which may be at near vacuum. In this or another embodiment, the condenser unit 301 may preferably comprise a horizontal condenser 300. The condenser 300 may be cooled by a thermal component. For example, the condenser 300 may comprise a body that is jacketed. The jacket may define an interior volume through which thermal medium comprising a cooling fluid may be provided to cool a condenser path within the body through which the gas and steam is flowed. The cooling fluid may be provided at a temperature between approximately room temperature and approximately −50° F.

The condenser 300 may be configured to receive the gas and steam and selectively condense the gas and steam for separation of solvent from the crude extract. For example, the gas and steam may be flowed through the condenser 300 to separate the pay material from solvent. The condenser 300 may separate the pay material from water and solvent, thereby, demulsifying and dewatering the extraction mixture. In various embodiments, the condenser 300 may recapture solvent and some of the lower boiling point terpenes for reuse later by the extraction system 10. For example, recaptured solvent may be returned to a solvent storage tank for reuse in further extractions. In some embodiments, the condensate produced along an initial cooled portion of the condenser 300 is collected as the solvent and lighter terpenes and the condensate produced along a subsequent cooled portion of the condenser 300 is collected as the crude extract. In further embodiments, the condensate collected along the initial portion of the condenser 300 may be further separated such that condensate produced along a first portion of the initial portion is collected as the lighter terpenes and the condensate produced along a second portion of the initial portion is collected as the solvent. Accordingly, these low weight terpenes may be captured and returned to the pay material during or after the process. For example, the terpenes may be added to refined pay material collected following short-path distillation.

Utilization of a condenser unit 301 comprising an in-line condenser demulsifier separator in the extraction process allows the extraction system 10 to accept wet plant material. For example, use of a horizontal condenser after the extraction vessel 200 reduces water content before winterization, thereby saving processing costs.

Transport component 16 may define one or more fluid paths fluidically coupled to the condenser unit 301 to receive and transport a solvent portion of the condensate for reuse or disposal. In some embodiments, transport component 16 transports the solvent to a solvent storage tank.

Transport component 18 may define one or more fluid paths fluidically coupled to the condenser to receive and transport the condensate comprising the crude extract, or pay material, to the winterization unit 400. In some embodiments, transport component 18 includes a fluid path for collecting the light terpenes condensed within the condenser. Transport component 18 may transport these terpenes to a terpene storage tank or to refined product storage tanks, for example. Transport components 16, 18 may also include one or more pumps or valves for controlling flow of condensate. In one embodiment, transport component 18 includes a storage vessel for storage of the pay material prior to transport to the winterization unit 400.

The winterization unit 400 may comprise an inline winterization unit to separate glycerin and organic wax from the pay material. Thus, the winterization unit 400 may winterize and dewax the pay material. The winterization unit 400 may decrease the temperature of the pay material and then filter the low temperature pay material to separate the glycerin and organic wax. The winterization unit 400 may include a vessel having an interior volume through which the pay material moves. The winterization unit 400 may further include a thermal component comprising a refrigerant system configured to extract thermal energy from the pay material as the pay material is flowed within the interior volume to thereby reduce the temperature of the pay material. The thermal component may include a jacket lining the winterization unit or flow paths through which the pay material is flowed, for example. In one example, the pay material exits the condenser at a temperature between 220° F. and 100° F., such as between 160° F. and 120° F., and is flowed through the winterization unit 400 wherein the temperature of the pay material is reduced to approximately −20° F. to −50° F., such as approximately −30° F. The abrupt drop in temperature may drive solidification and/or agglomeration of glycerin and waxes. The winterization unit 400 may include filters through which the cool pay material is filtered to remove the glycerin and wax. Wax and glycerin removal prior to further extraction processing prevents buildup or gumming up and/or the breaking down of sub-process equipment further down the line.

Transport component 20 may define one or more fluid paths to receive the pay material from the winterization unit 400 and transport the pay material to a filter unit 500. In one example, Transport component 20 may include one or more pumps to assist in transport or one or more storage vessels to store the winterized pay material prior to transport to the filter unit 500.

Transport component 20 may transport the winterized pay material to the filter unit 500 wherein the pay material is further filtered. Filter unit 500 is configured to remove particulates from the pay material to the micron. In various embodiments, the filter unit 500 includes a press filter or vibratory shear enhancing process (VSEP) filter unit. The filters through which the cool pay material is passed with respect to the winterization unit 400 preferably filter larger particles to maintain a consistent flow through the filters and filter unit 500. For example, filtering in winterization with larger filters for winterization may reduce clogging events or filter cleanings compared to use of smaller filter sizes. However, in one embodiment, the extraction system 10 does not include filter unit 500 and transport component 20 transports pay material from the winterization unit 400 to the preheater 600. It will be appreciated that in some embodiments, the filter unit 500 may be an extension of the winterization process to include additional filters for filtering progressively smaller particles.

Transport component 22 may define one or more fluid paths to receive the pay material from the filter unit 500 and thereafter transport the pay material to a preheater 600. In one example, transport component 22 may include one or more pumps to assist in transport or one or more storage vessels to store the pay material prior to transport to the preheater 600.

The preheater 600 is positioned to receive the pay material from transport component and heat the pay material prior to cannabinoid extraction at the short-path distillation unit 700. The preheater 600 may heat the pay material to achieve temperature control and optimize subsequent recovery of the temperature sensitive cannabinoids. For example, the preheater 600 may heat the pay material to between approximately 100° F. and approximately 220° F. In some embodiments, the temperature to which the preheater 600 heats the pay material may correspond to an evaporation temperature with respect to the separation targeted in the short-path distillation unit 700. In various embodiments, the preheater 600 may heat the pay material to a temperature between approximately 120° F. and 160° F., approximately 140° F. and approximately 200° F., or approximately 160° F. and approximately 220° F. The temperature of the preheater 600 and the flow of the pay material may be controlled to achieve precise temperature control of the pay material to between +/−10° F., +/−5° F., +/−2° F., or +/−1° F., for example.

Transport component 24 may define one or more fluid paths to receive the pay material from the preheater 600 and transport the pay material to the short-path distillation unit 700. Transport component 24 may also include one or more pumps to assist in transport.

The pay material may be fed into the short-path distillation unit 700 for separation of pay material constituents. The short-path distillation unit 700 may be configured for molecular distillation. The short-path distillation unit 700 may include a vessel having an interior volume through which pay material is flowed. The short-path distillation unit 700 may include a thermal component for heating the vessel, e.g., a heater or jacket through which a heated fluid may be flowed. In some embodiments, the short-path distillation unit 700 comprises a thin film or wiped film evaporator. The pay material may be fed into the interior volume or evaporation chamber and distribute along a heated wall or heated surface within the interior volume. Wiper blades may be movable within the interior volume to agitate or work the film of pay material along the surface. Exposure to the heated surface in the low-pressure environment may result in selective evaporation of solvent and pay material components. In one embodiment, configurations such as falling or rising film evaporators may also be used. In one embodiment, the short-path distillation unit 700 may comprise an agitated film evaporator or a short-path evaporator comprising a cold condensation surface within the interior of the vessel to capture and condense gas and steam evolving from the heated surfaces, which may define the outer perimeter of the interior volume of the vessel proximate to the condensing surface. The short-path distillation unit 700 may be configured to isolate and then send the isolate to the appropriate vessels as needed. For example, the vessel may include one or more, such as multiple, discharge ports for multiple receiving tanks for receiving refined isolates having specific compositions, such as cannabinoids by weight. The evaporation chamber may be at low-pressure, such as less than approximately −5 psi, less than approximately −10 psi, or lower.

The short-path distillation unit 700 may be configured with a recirculating loop for refining multiple passes. For example, the short-path distillation unit 700 may be configured with a recirculating loop to recirculate extracted material for isolating specific cannabinoids for separation or for multiple passes. After a first pass-through at a first setting, the first run material may be deposited into a vessel and then the remaining material may be recirculated back for one or more second pass-throughs at a different settings. In some embodiments, the recirculation loop may include the preheater 600. For example, pay material for recirculation may be collected and stored in a pay material recirculation tank prior to recirculation. The settings parameters may include, e.g., temperature, pressure, flow rate, and/or wiper rate. For example, increase in temperature may result in evaporation of higher weight components. To counter thermal loss during residence time in the pay material recirculation tank, the pay material may also be recirculated through the preheater 600 prior to recirculation through the short-path distillation unit 700. In some embodiments, a valve may be used to route the pay material along transport lines for recirculation through the preheater 600 or to bypass the preheater 600 before recirculation through the short-path distillation unit 700. In some embodiments, temperature sensors 1020a may measure the temperature of the pay material for recirculation and send the measurements to the controller 1010. The controller 1010 may determine if preheating in necessary and, if so, actuate the value to route the pay material through the preheater 600. The controller 1010 may also determine heating temperature of the preheater 600 in order to heat the pay material to the desired temperature for the particular weight separation desired during the recirculation through the short-path distillation unit 700.

The unevaporated material from the short-path distillation unit 700 or condensed material from the condenser unit 801 may be collected and passed through the same or a different short-path distillation unit 700. The temperature of the short-path distillation unit 700 during the subsequent pass may be higher or lower to target evaporation of lower or higher weight cannabinoids. This may be repeated to obtain the desired separation of cannabinoids. Changes in temperature may be provided by higher temperature thermal medium, flow rate of thermal medium, and/or wiper rate, for example.

As introduced above, the short-path distillation unit 700 may include multiple short-path distillation units 700 aligned in series, each configured to separate/evaporate a particular weight or weight range of component in the pay material. The short-path distillation unit 700 may also include multiple short-path distillation units 700 arranged in parallel defining multiple distillation paths that may be separate or converging at one or more points along the path. For example, a temperature or temperature range may be set for a particular unit to evaporate a weight or weight range of component. For example, the cannabinoid tetrahydrocannabinol (THC) has a boiling point of 157° F. and maybe evaporated within the evaporation chamber at lower temperatures due to a low-pressure environment and increased exposure to surrounding air within the evaporation chamber. This temperature for evaporation at the same pressure is lower than heavier cannabinoids such as cannabidiol (CBD) and tetrahydrocannabivarin (THCV), which have boiling points of 160° F.-180° F. and 220° F., respectively. Thus, subsequent increased temperatures may be used to evaporate higher weight cannabinoids, while still heavier cannabinoids pass through the evaporation chamber.

The evaporated components may be subsequently condensed in the condenser unit 801, which may include a plurality of condensers 800 each associated with one or more of the short-path distillation units 700. For example, the condenser unit 801 may include multiple condensers 800 aligned in series, each configured to separate/condense a particular weight or weight range of component in the pay material. The condenser unit 801 may also include multiple condensers 800 arranged in parallel defining multiple condensation paths that may be separate or converging at one or more points along the path. The condensed component may then be collected. In some embodiments, the collected condensed component may be further refined by processing in one or more additional short-path distillation units and condensers. The pay product may include one or both of the material that fails to evaporate within the evaporation chamber or the condensate obtained in the condenser unit 801.

In some embodiments, one or more manifolds may be positioned before or after one or more short-path distillation units 700. For example, transport component 24a or intermediate transport components may include manifolds for distributing outputs of the short-path distillation unit 700 and/or condenser unit 801. Plant material may be distributed from the manifold to two or more short-path distillation units 700 or series or paths of distillation units configured to separate/evaporate a particular weight or weight range of component in the pay material. Similarly, additional manifolds may be positioned after the short-path distillation units 700 or within a series or path of distillation units to further distribute the unevaporated pay material or condensed pay material for further separation.

Transport component 26 may define one or more fluid paths to receive the pay material from the one or more discharge ports of the short-path distillation unit 700 and transport the pay material to one or more pay material receiving tanks. As noted above, the short-path distillation unit 700 may include multiple discharge ports, thus, transport component 26 may include separate flow paths for transporting the pay material received from each discharge port to a separate pay material tank. In some embodiments, however, transport component 26 may define two or more flow paths that converge to combine pay materials. In one embodiment, the transport component 26 may be used to collect fractions comprising select refined cannabinoids and/or other pay material components. One or more pumps may be used to assist in transport of the pay material.

Transport component 28 may define one or more fluid paths positioned to receive gas and steam from the short-path distillation unit 700 and transport the gas and steam into an interior volume of to the condenser 800. The condenser unit 801 may be located proximate to the short-path distillation unit 700. In various embodiments, condenser unit 801 comprises a vertical condenser 800. The condenser unit 801 may include a thermal component such cooling surfaces and/or a jacket lining for condensing the gas and steam flowed through the interior volume of the condenser 800. The condenser 800 may be at low-pressure, such as less than approximately −5 psi, less than approximately −10 psi, or lower. The condenser unit 801 may separate remaining solvent and extracted pay material. Transport component 30 may define one or more fluid paths for receiving condensate comprising separated solvent and one or more fluid paths for receiving condensate comprising separated pay material. The respective fluid paths may transport the condensates to solvent and product tanks.

In various embodiments, the extraction system 10 further includes a vapor-liquid separator. For example, a transport component defining a fluid path may be positioned to receive any remaining material from the condenser unit 801 and transport the material to the vapor-liquid separator for collection. The vapor-liquid separator may be temperature controlled to ensure uniform recovery of terpenes and other liquids. For example, a temperature controlled vapor-liquid separator may be used to remove remaining solvents and condense other remaining gases, e.g., terpenes, for recovery. The recovery may be reused as described above and elsewhere herein, such as by addition to collected pay products. In one embodiment, the short-path distillation unit 700 comprises a vapor-liquid separator upstream of the condenser unit 801, which may be in addition to or instead of a downstream vapor-liquid separator. As used herein, a vapor-liquid separator may include or alternatively be a liquid-gas separator.

As introduced above and described in greater detail below with respect to FIGS. 2-11, the extraction system 10 may include thermal components for thermal maintenance of one or more processing environments, transport environments, or both of the extraction system 10. In various embodiments, the extraction system 10 controls temperature from the moment the plant material 12 enters the extraction vessel 200 and throughout the entire process to obtain refined pay material. For example, all vessels and plumbing such as transport components and lines may be temperature controlled. In some embodiments, sub-process equipment may be positioned proximate to subsequent sub-process equipment that maintenance or change in temperature of the transient pay material is unnecessary. For example, in some embodiments, transport lines between the condenser 300 and winterization unit 400 may be temperature controlled to maintain a pay material temperature within the transport lines above approximately 100° F., above approximately 110° F., above approximately 120° F., or above approximately 130° F. Maintaining temperature above such minimums may promote sudden temperature drop at the winterization unit 400. In one embodiment, transport component 20 and/or transport line 20a, 20b may be configured to prevent temperature of the pay material from rising above a predetermined maximum temperature. In this or another embodiment, one or more of transport components 22, 24 and/or transport lines 22a, 22c, 24a may be temperature controlled to maintain pay material temperature within the lines above a predetermined temperature. In some embodiments, transport components and lines may be configured to impart heat to the pay material as it is flowed there-through. In one example, such transport components and lines may assist or replace preheater 600. It will be appreciated that in some embodiments preheater 700 may be associated with a storage tank, such as storage tank 22b or another storage tank, wherein the pay material is heated prior to being passed to the short-path distillation unit 700. In one embodiment, storage tank 22b may be configured with a heater, e.g., thermal coils, jacket, or other heater configuration, to heat the pay material prior to the preheater 600. In some embodiments, all plumbing may not be temperature controlled. Various embodiments including a storage tank 22b may include multiple storage tanks 22b that receive pay material from one or more winterization units 400 or filter units 500.

Further to the above, maintaining optimal processing and transport temperatures provides a tight temperature control to limit unwanted burn off and limit pay material degradation. In some embodiments, the extraction system 10 is temperature controlled from end-to-end utilizing thermal components comprising jacketed processing components and transport components. Jacketed may include heat exchange/transfer between thermally conductive materials defining the flow path through which the pay material passes. Thus, in some embodiments, lines, passages, or coils through or over which thermal fluid may be flowed and/or electric heaters may be positioned adjacent to pay material flow paths. Steam, oil, liquid, fluid, or other medium may be used to control temperature, for example. The extraction system 10 may therefore be scalable, temperature controlled, which may be from end-to-end, with heating and cooling, configured for recapture of solvent and terpene organically, arranged with in-line winterization and dewaxing, and configurable to extract and isolate cannabinoids at their weight through short-path distillation. As noted above, active temperature control may not be necessary at one or more points along the transport paths between the sub-process equipment, e.g., due to proximity between certain sub-process equipment or where degradation is not a concern.

Sound and solvents may be used with in-line condensers and vapor-liquid separators that are automated using the control system and without chemicals. The extraction system 10 may utilize low-pressure and negative atmosphere at certain parts of the process without chemicals, which leads to a safer working environment. The extraction system 10 may be configured to operate without purging any liquids and/or gases and rather separate constituents by negative atmosphere and then store them in appropriate vessels. The extraction system may also be a closed system from end to end. This may ensure that any vapors or gases remain in the proper vessels and are not released into the atmosphere where the vapors may explode. In preferred embodiments, steam is not introduced to the product as steam is detrimental and causes degradation of the product.

As noted above, the extraction system 10 may process cannabis oil without chemicals. For example, dewatering may take place in-line through automated equipment. For example, condenser 300 may be a horizontal condenser which separates like gases comprising terpenes, solvents, and pay material without the use of chemicals.

The extraction system 10 may include completely integrated extraction apparatuses and processing and all in one processing automation and temperature control throughout the process. The extraction system 10 may also avoid the use of decarboxylation. Solvent may be removed without chemicals through the use of condenser unit 301 comprising a horizontal condenser, condenser unit 801 comprising a vertical condenser, and a vapor-liquid separator after the vertical condenser. Filtration may also be in-line and automated via filter unit 500 comprising a micron filter, e.g., micron press filter or VSEP filtration unit. The in-line filter unit 500 may be used to ensure that all particulates are removed so that only cannabis oil and remaining solvent enters the wiped film extractor.

Figure 2:
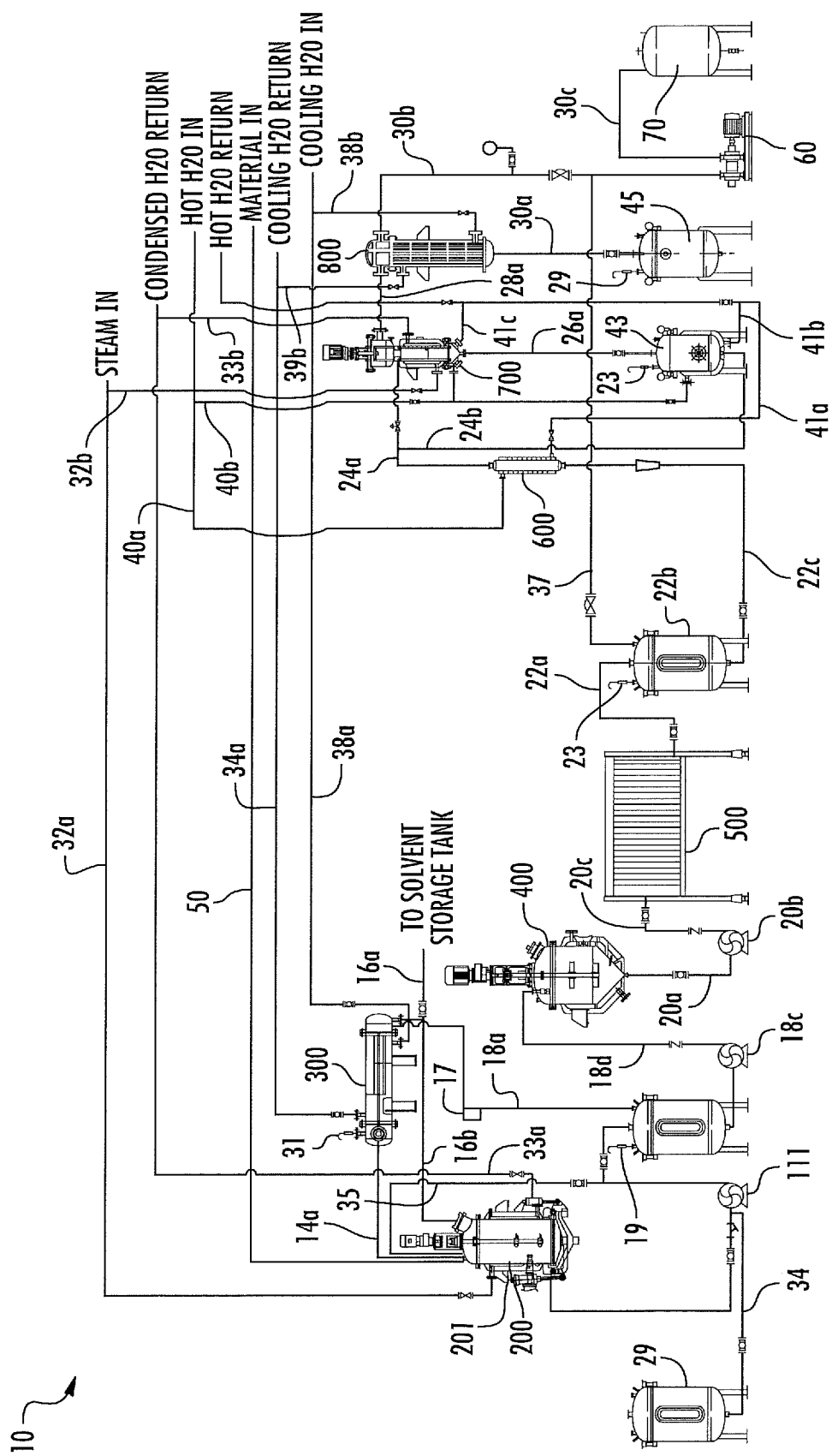
FIG. 2 is a schematic diagram of an extraction system according to various embodiments described herein.

FIG. 2 schematically illustrates a further embodiment of the extraction system 10 described with respect to FIG. 1. The extraction system 10 includes sub-process units comprising an extraction unit 201 comprising one or more extraction vessels 200, a first condenser unit 301 comprising one or more condensers 300, a winterization unit 400, a filter unit 500, a preheater 600, a short-path distillation unit 700, and a second condenser unit 801. FIGS. 3-9 illustrate enlarged cross-section views of these sub-process units according to various embodiments.

Figure 3:
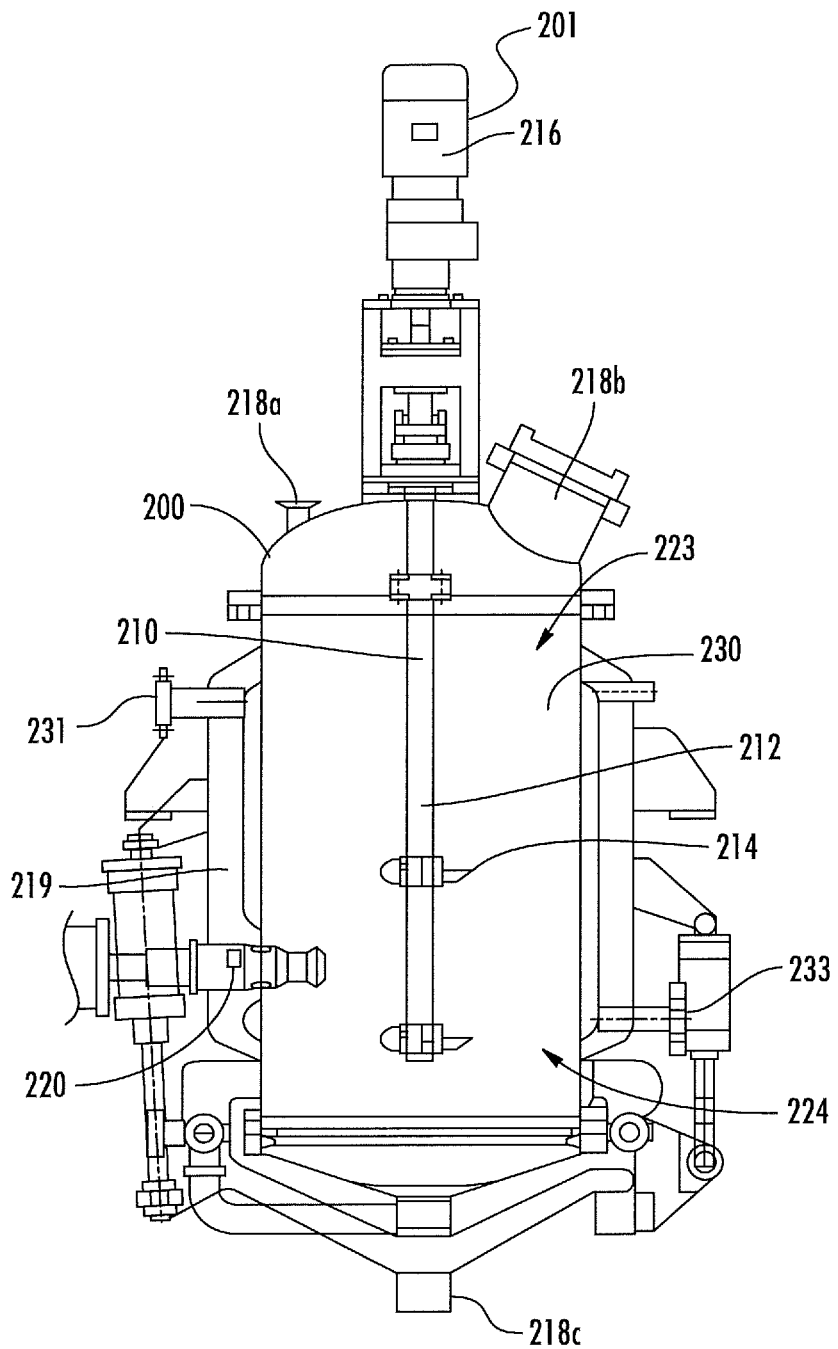
FIG. 3 illustrates an extraction vessel of the extraction system according to various embodiments described herein.

With specific reference to FIG. 2 and FIG. 3, plant material may be delivered to the extraction vessel 200 via the feed delivery subsystem 50, which may include, for example, one or more of a pipe, hopper, chute, belt, auger, or combinations thereof along which plant material is transported to the extraction vessel 200.

The extraction vessel 200 defines an interior volume 230 for containing solvent and plant material. The extraction vessel 200 also includes a thermal component for providing heat to the interior volume 230. As shown in FIG. 3, a jacket 219 is provided for temperature control with a thermal medium. In this embodiment, the thermal medium comprises steam; however, in other embodiments other thermal mediums may be used, such as oil, steam, water, gas, or other suitable medium, including those described elsewhere herein. The steam may be delivered to the jacket 219 through thermal delivery line 32a. The steam may enter the jacket 219 via thermal input port 231 and flow therein until discharged from thermal output port 233. The discharged thermal medium, which may be condensed water, may be returned to heaters or steam generators for reheating via thermal return line 33a.

The extraction vessel 200 also includes a plurality of ports for receiving and discharging processing materials with respect to the interior volume 230. The plant material may be delivered into the interior volume 230 through a plant material loading port. Extraction vessel 200 includes port 218a comprising one or more ports provided at an upper end 223 of the extraction vessel 200. In this embodiment, port 218a comprises a plant material loading port 218a. In other embodiments, the extraction vessel 200 comprises a plant material loading port along a lower end 224 of the extraction vessel 200.

The extraction system 10 may include or be configured to receive a supply of solvent. In the illustrated embodiment, the extraction system 10 includes a solvent storage tank 29 for containing a supply of solvent. Transport components comprising lines 34, 35 may fluidically couple the solvent storage tank 29 and the extraction vessel 200. A pump 111 may be provided for pumping solvent along the lines 34, 35 to a solvent loading port, generally identified as port 218a, or a port thereof. In another embodiment, the extraction vessel 200 may include a solvent loading port along lower end 224. The solvent loaded into the extraction vessel 200 through the solvent loading port may flow into the interior volume 230 of the extraction vessel 200. Pump 111 or another pump may be used to evacuate the extraction vessel and provide a low-pressure environment for the extraction process as described above and elsewhere herein. For example, pump 111 may be in fluid communication with the interior volume 230 and operable therethrough to generate vacuum. Pump 111 may couple to the interior volume 230 through an evacuation port, generally identified as port 218a, or a port thereof. For example, pump 111 may reduce pressure within the interior volume 230 through line 34 and port 218a. Valves may be used to control flow through the various transport component lines for transporting processing materials, thermal mediums, and generating low-pressure environments. As introduced above, a control system may be operable to actuate valves and pumps to control various extraction processes.

A mechanical agitator 210 comprising an agitation member 212 extends into the interior volume 230. One or more extensions 214 may further extend from the agitation member 212 and to engage a column of plant material and/or solvent within the interior volume. In the illustrated embodiment, the mechanical agitator 210 is mounted in the center of the interior volume 230 of the extraction vessel 200 to move the plant material 12 evenly through the duration of the oil extraction from the plant material 12. A motor 216 is operably connected to the agitation member 212 to transfer rotation to the agitation member 212.

A transducer 220 is positioned to direct soundwaves into the interior volume 230. The transducer 220 may be positioned for even disbursement of soundwaves throughout the biomass column within the interior volume 230. The transducer 220 may be a variable frequency transducer as introduced above and described elsewhere herein. The transducer may be movably mounted for changing the direction of soundwave emission from the transducer 220. The transducer 220 may be pivoted vertically and/or horizontally, for example. As shown, the transducer 200 is positioned along, e.g., extends from or through, a side perimeter or sidewall defining the interior volume 230. As noted above and elsewhere herein, multiple transducers 220 may be positioned along the perimeter of the interior volume 230. For example, one or more rows of transducers 220 may be positioned along the perimeter. The transducers 220 may be aligned, staggered, or both. In some embodiments, one or more transducers 220 are positioned along or extend through a bottom perimeter or bottom wall defining the interior volume 230 to direct soundwaves upward through the interior volume 230. Such transducers 220 may be in addition to or instead of one or more transducers 220 positioned along a side perimeter or sidewall of the interior volume 230.

In operation, the mechanical agitator 210 and transducer 220 agitate the solvent and plant material. The extraction vessel 200 may also provide a low-pressure and elevated temperature environment within the interior volume 230 during or following agitation. For example, the plant material and solvent mixture may be agitated by the mechanical agitator 210 and disrupted by the soundwaves emitted by the transducer 220 in a heated and low-pressure environment to promote transition of the mixture into vapor and steam components. As introduced above, the low-pressure reduces boiling points required for vaporization and reduces cannabinoid burn off and degradation. Low-pressure may include vacuum or negative atmosphere pressures.

The extraction vessel 200 may include a discharge port for gas and steam to discharge from the interior volume 230. In the embodiment shown in FIG. 3, discharge port is generally identified as port 218a, or a port thereof positioned along the upper end 223. Steam and gas may discharge from the interior volume through port 218a and flow along a transport component comprising line 14a to condenser 300 for demulsifying separation and dewatering.

An additional port (not visible) may also be provided at the upper end 222 of the extraction vessel 200 for discharge of gas and steam comprising pay material and solvent.

A discharge port may be provided at a lower end 224 of the extraction vessel for discharge of remaining biomass following extraction. For example, the extraction vessel 200 may include port 118c and be configured to discharge the remaining biomass from the interior volume 230 through port 118c. The discharged biomass may discharge into discharge line 36.

Figure 4:
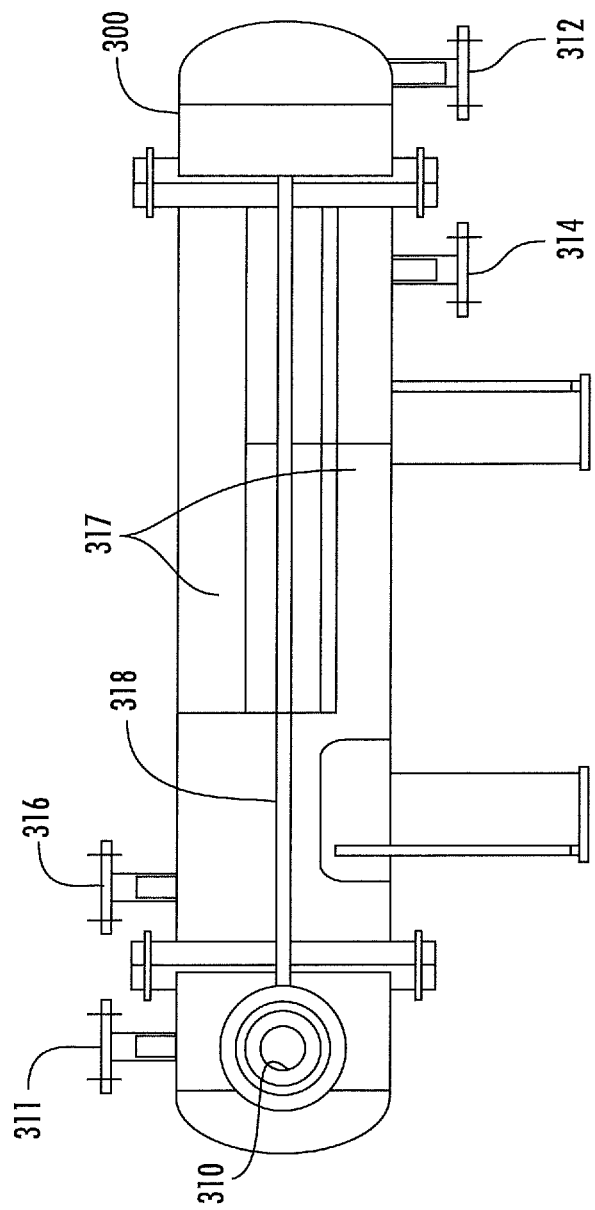
FIG. 4 illustrates a condenser unit of the extraction system according to various embodiments described herein.

With continued reference to FIG. 2 and further reference to FIG. 4, illustrating a cross-section of the condenser 300 of the condenser unit 301 according to various embodiments, condenser unit 301 may comprise a horizontal condenser 300 configured for demulsifying separation and dewatering of the extract and solvent mixture.

Condenser 300 includes a jacketed 317 for temperature control. The jacket 317 jackets an interior flow path 318 that extends through the condenser 300. The extraction system 10 includes or is configured to couple to a supply of thermal medium comprising chilled water or another cooling fluid. In the illustrated embodiment, cooling water is transported along a transport component comprising thermal delivery line 38a and is delivered into the condenser jacket 317 through thermal input port 316. The cooling water may flow through the jacket 317 and discharge from thermal output port 316. The gas and steam comprising the solvent/extract mixture may be provided into the condenser 300 from line 14a through feed port 310. In some embodiments, the condenser 300 may include a coupling line 31 to couple multiple condensers 300 and/or multiple extraction vessels 200. For example, multiple extraction vessels 200 may feed condenser 300. In this or another example, multiple condensers 300 may receive gas and steam from one or more extraction vessels 200. Coupling line 31 may input at feed port 311. In some embodiments, input port 310 and input port 311 comprises the same port.

As introduced above, condenser unit 301 may be configured for demulsifying separation to recover lighter terpenes, solvent, and pay material as well as separate water. Solvent is recovered and sent via transport component to the solvent tank 29 from discharge port 312 for disposal or reuse in subsequent extractions. The transport component is illustrated as line 16a. In some embodiments, line 16a comprises multiple lines for transporting different solvents or solvent blends to different solvent storage tanks 29. In some applications, recovered solvent may be returned to the extraction vessel 200. For example, the extraction vessel 200 may further include a solvent return port for receiving condensed solvent from the condenser 300. For example, the solvent return port may include a port positioned along the upper end 223 or lower end 224 of the extraction vessel 200, such as port 218a, 218b. In the illustrated embodiment, condensed solvent may be returned to the extraction vessel 200 through a transport component comprising line 16b and be delivered into the interior volume through port 218b. However, in other embodiments, there is not a condensed solvent return directly to the extraction vessel 200 and all condensed solvent is transported to a solvent storage tank or for disposal. It will be appreciated that the particular uses identified for the illustrated ports may be rearranged. For example, port 218b could be used for inputting feed material into the interior volume 230 of the extraction vessel 200.

The recovered terpenes are similarly recovered for reuse later. These terpenes may be discharged from the condenser 300 via a discharge port, which is not visible in the depicted cross-section. These terpenes may be transported using one or more transport components to one or more terpene storage containers or directly to storage tanks containing refined extract. For example, the light terpenes recaptured by the condenser 300 may be collected and stored for future use together with or separate from the extract or another extract or may be recombined with the extract or another extract following refinement.

The separated portion of the mixture comprising the pay material may be discharged through a pay port (not visible in the illustrated cross-section) and transported through a transport component comprising line 18a to the winterization unit 400 for dewaxing. In the illustrated embodiment, the transport line 18a includes a visualization portion 17 comprising a sight glass or transparent tube or portion thereof that allows a user to observe the material passing from the condenser along line 18a. In some embodiments, the transport line 18a may include an analysis portion comprising a sensor 1022 (see FIG. 11), such an optical sensor, may be positioned to measure one or more characteristics of the material. For example, the sensor may detect transparency or employ absorption spectroscopy to analyze the material. The controller 1010 may generate a warning when characteristics of the material are outside threshold parameters determined from an operation program, for example. Some embodiments may not include a visualization portion 17 and/or an analysis portion.

In the illustrated embodiment, the transport component also includes a pay material storage tank 18b for storing pay material prior to dewaxing. In other embodiments, the pay material may be transported directly to the winterization unit 400. The pay material storage tank 18b may include a coupling line 19 to couple multiple pay material storage tanks 18b and/or multiple condensers. For example, multiple pay material storage tanks 18b may hold the pay material transported through line 18a. One or more of those pay material storage tanks 18b may also receive pay material from one or more other condensers 300. In some embodiments, coupling line 19 may receive pay material from additional condensers 300. A pump 18c is provided for transporting pay material from the pay material storage tank 18c, through line 18d, to the winterization unit 400. Separated water that is condensed in the condenser 300 may be collected and transported by a water transport line (not shown) to a water storage tank or for disposal.

Figure 5:
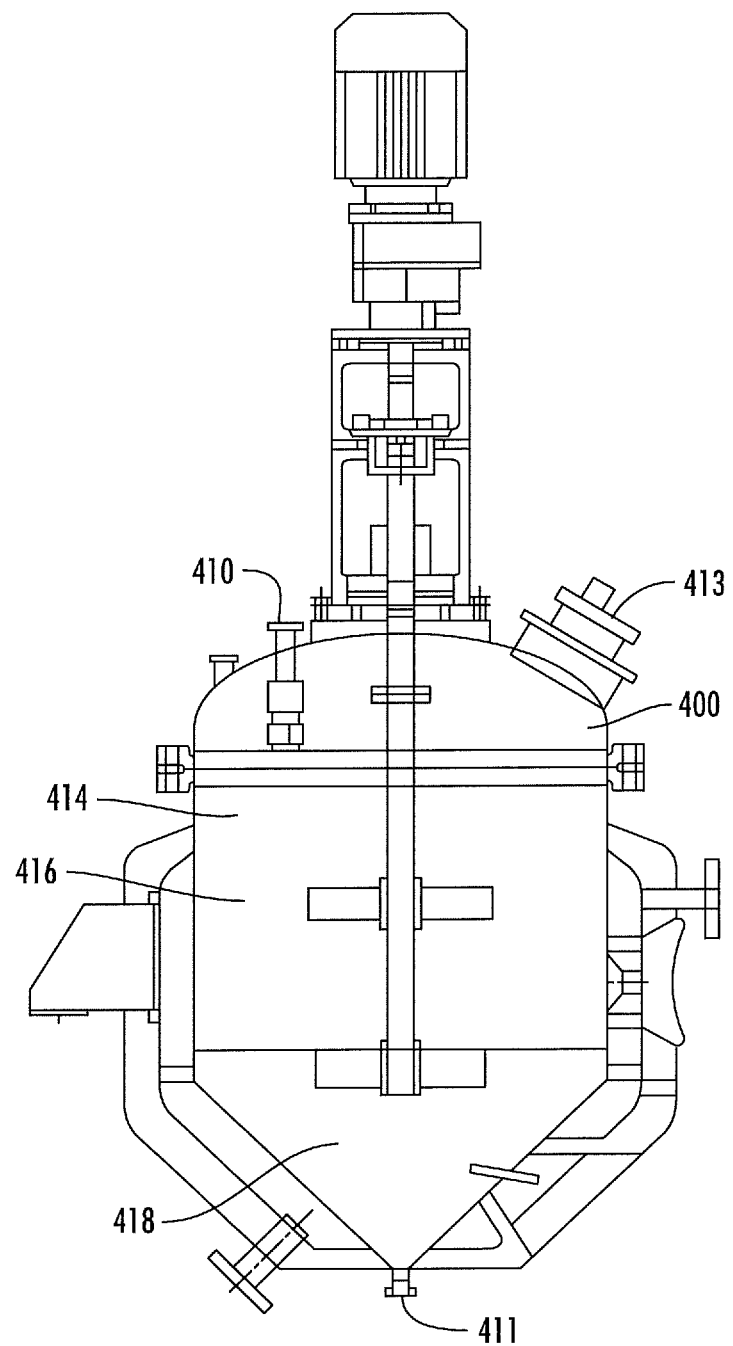
FIG. 5 illustrates a winterization unit of the extraction system according to various embodiments described herein.

With continued reference to FIG. 2 and further reference to FIG. 5, illustrating a cross-section of the winterization unit 400 according to various embodiments, the winterization unit 400 may comprise an inline winterization and dewaxing unit to separate glycerin and organic wax directly from the pay material. The winterization unit 400 unit includes a feed port 410 for receiving the pay material and a pay port 412 for discharging the winterized pay material.

The winterization unit 400 includes a flow path 414 through which the pay material is flowed. Walls 416 defining the flow path are chilled to low temperatures, e.g., between −20° F. and −50° F. or colder, to extract heat from the pay material. Pump 18c, 20a, and/or another pump may be used to flow the pay material along the flow path. The flow path may include a series of filters or screens through which the low temperature pay material is passed to collect various waxes, fats, and glycerin. In some embodiments, the walls 416 defining the flow path are chilled by a refrigerant system. In one example, the winterization unit 400 rapidly cools the pay material from a temperature between 220° F. and 100° F., such as between 160° F. and 120° F., to approximately −20° F. to −50° F., such as approximately −30° F. In other embodiments, the pay material may be delivered into the winterization unit 400 at lower temperatures, such as when the pay material has undergone an extended residence within the pay material storage tank 18b. The reduction in temperature causes solidification and/or agglomeration of glycerin and waxes. The winterization unit 400 may further include a plurality of filters 418 positioned along the flow path to filter the pay material and thereby remove the glycerin and wax.

The winterized pay material may be discharged from the winterization unit 400 through pay port 12 and subsequently transported by a transport component comprising line 20a, pump 20b, and line 20c to the filter unit 500.

Figure 6:
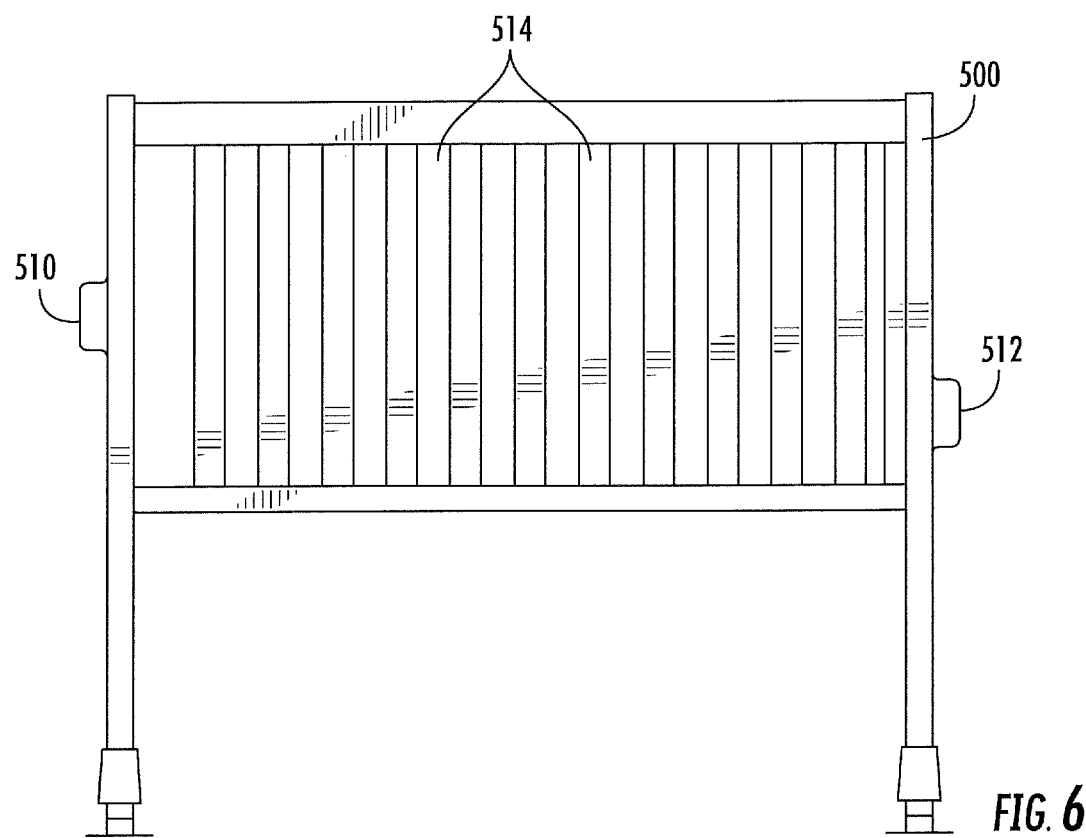
FIG. 6 illustrates a filter unit of the extraction system according to various embodiments described herein.

With continued reference to FIG. 2 and further reference to FIG. 6, illustrating filter unit 500 according to various embodiments, the filter unit 500 may be configured to remove particulates to the micron. The filter unit 500 comprises a press filter configuration. Pay material is fed into the filter unit 500 through a feed port 510. The filter unit 500 includes plates 516 between which the pay material may be filtered during the press filtering process. The filtered pay material may discharge from the filter unit through pay port 514. As noted above, other filtration units 500 may be used, such as a VSEP Filter.

Transport component 20 may transport the winterized pay material to the filter unit 500 wherein the pay material is further filtered. Filter unit 500 is configured to remove particulates from the pay material to the micron. In various embodiments, the filter unit 500 includes a press filter or vibratory shear enhancing process (VSEP) system. The filters through which the cool pay material is passed with respect to the winterization unit 400 preferably filter larger particles to maintain a consistent flow through the filters and filter unit 500. For example, filtering in winterization with larger filters for winterization may reduce clogging events or filter cleanings compared to use of smaller filter sizes. However, in one embodiment, the extraction system 10 does not include filter unit 500 and transport component 20 transports pay material from the winterization unit 400 to the preheater 600. It will be appreciated that in some embodiments, the filter unit 500 may be an extension of the winterization process to include additional filters for filtering progressively smaller particles.

After being discharged from the filter unit 500, a transport component may transport the pay material to the preheater 600. In the illustrated embodiment, the transport component comprises line 22a, pay material storage tank 22b, and line 22c. In some embodiments, pay material may be transported directly to the preheater 600 from the filter unit 500. As noted above, in some embodiments, the extraction system 10 does not include a filter unit 500, in one such embodiment, the pay material is transported to the pay material storage tank 22b prior to transporting the pay material to the preheater 600, while in another embodiment the pay material is directly transported to the preheater 600 from the winterization unit 400. The pay material storage tank 22b may include multiple pay material storage tanks coupled by a coupling line 23. The pay material storage tanks 22b may receive pay material from one or more winterization units 400 or filter units 500. The winterization unit 400 may also include a port 413 for receiving pay material from additional storage tanks 18b, condensers 300, or transport lines 18a, 18c. In some embodiments, transport line 18a, 18c may couple to multiple storage tanks or condenser 300.

Figure 7:
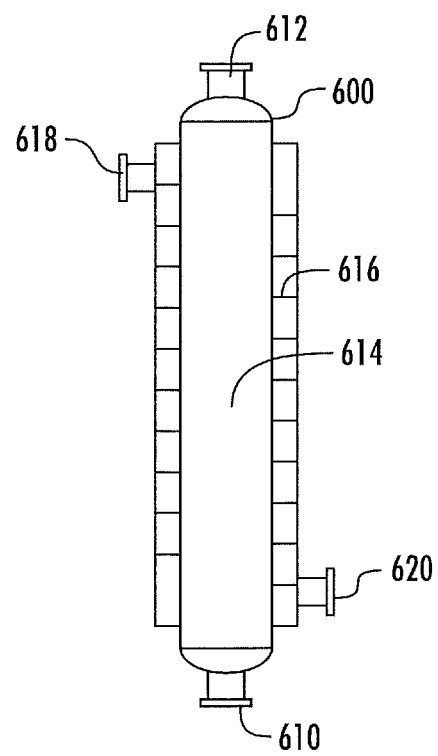
FIG. 7 illustrates a preheater of the extraction system according to various embodiments described herein.

With continued reference to FIG. 2 and further reference to FIG. 7, illustrating a cross-section of the preheater 600 according to various embodiments, the preheater 600 is positioned to receive the pay material from line 22c. The preheater 600 is configured to preheat the pay material prior to refining cannabinoid extraction at the short-path distillation unit 700. The preheater includes a feed port 610 for receiving pay material and pay port 612 for discharging preheated pay material. The pay material is flowed through an interior flow path 614 defined by the preheater 600. The preheater 60 includes a thermal component comprising a jacket 616 through which thermal medium may be flowed to heat the interior flow path 614, such as the walls 622 defining the interior flow path 614, and transfer the heat to the pay material.

As introduced above, the extraction system 10 includes or is configured to couple to one or more supplies of thermal medium comprising a hot fluid. The thermal medium may include a heated fluid such as hot gas, water, steam, or oil, for example. The supply of thermal medium may be the same or different than the supply used for other sub-process equipment and/or transport components. In the illustrated embodiment, the extraction system 10 includes or is configured to couple to a supply of thermal material comprising hot water. The water may be at a temperature from room temperature to boiling. The hot water may be transported through thermal delivery line 40a and supplied into the jacket 616 through thermal delivery port 618. The hot water may be flowed within the jacket 616 thereby heating the walls 622 defining the interior flow path 614. In the illustrated embodiment, the jacket 616 defines a helical path through which the hot water flows. In some embodiments, the jacket 616 defines other paths such as longitudinal chambers, for example. After passing through the jacket 616, the hot water is discharged through thermal discharge port 620 and may be flowed through thermal return line 41a for reheating and recirculation or discharge.

After processing through the preheater 600 the heated pay material is discharged from pay port 612 and transported to the short-path distillation unit 700 by a transport component comprising line 24a. In one embodiment, the preheater 600 may be integrated with an initial portion of the short-path distillation unit, prior to an evaporation chamber.

Figure 8:
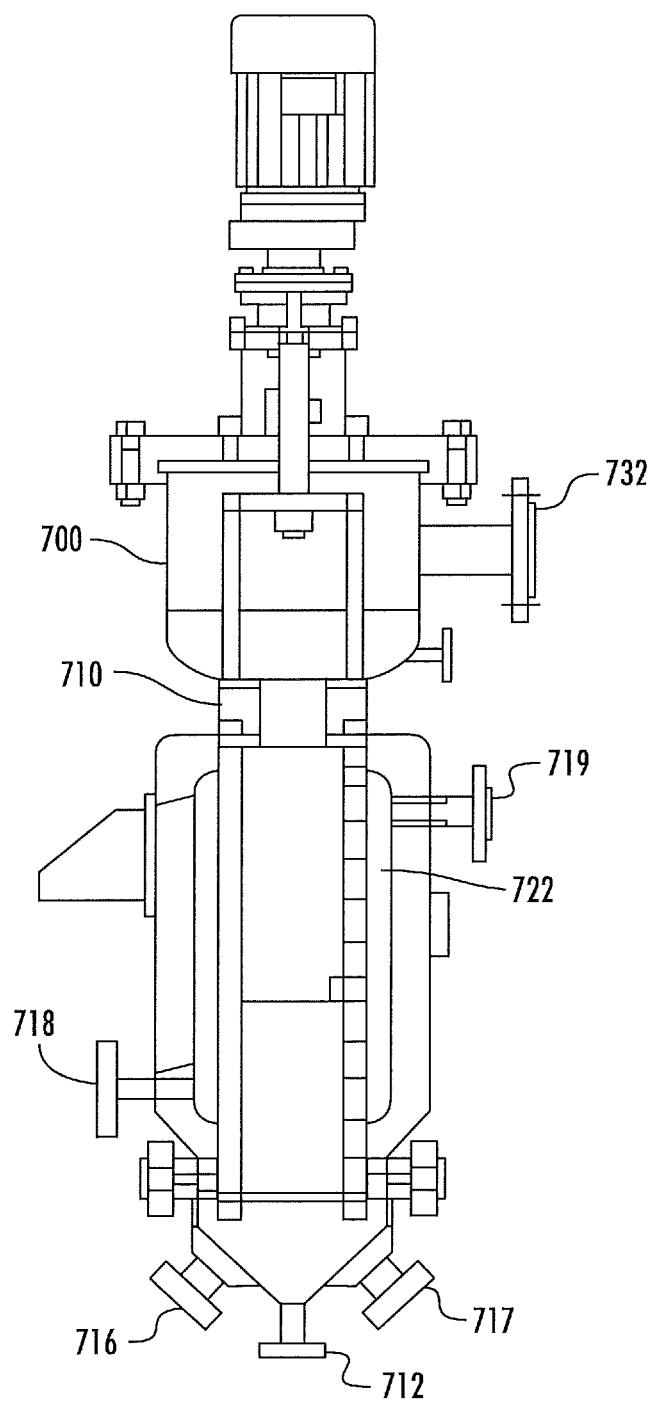
FIG. 8 illustrates a short-path distillation unit of the extraction system according to various embodiments described herein.

With continued reference to FIG. 2 and further reference to FIG. 8, illustrating a cross-section of the short-path distillation unit 700 according to various embodiments, the short-path distillation unit 700 may include a thin film or wiped film evaporator/distillation configuration. The preheated pay material may be fed into the short-path distillation unit 700 at a feed port 710 for separation of pay material constituents and removal of any remaining solvent. The short-path distillation unit 700 may include an interior volume comprising an evaporation chamber 720 through which pay material is flowed. The short-path distillation unit 700 may include a thermal component for heating the vessel, e.g., a heater or jacket 714, 715 through which a thermal medium may be flowed. The thermal medium may include a heated fluid such as hot gas, water, steam, or oil, for example. The supply of thermal medium may be the same or different than the supply used for other sub-process equipment and/or transport components. In the illustrated embodiment, the extraction system 10 includes or is configured to couple to a supply of a first thermal material comprising hot water and a supply of a second thermal material comprising steam. The hot water may be transported through thermal delivery line 40b and supplied into the lower jacket 714 through thermal delivery port 716. The hot water may be flowed within the jacket 714 and discharged as condensed water at thermal discharge port 717. The hot water may them be transported along thermal return line 41c for reheating and recirculation or discharge. The steam may be transported through thermal delivery line 32b and supplied into the upper jacket 715 through thermal delivery port 718. The steam may be flowed within the jacket 715 and discharged as condensed water at thermal discharge port 719. The condensed water may them be transported along thermal return line 33b for reheating and recirculation or discharge. The steam may be used to heat a surface 722 onto which a thin film of the pay material is distributed. As shown in the illustrated embodiment, the short-path distillation unit 700 may be configured to include two separate thermal heating paths. The separate paths may receive separate or different thermal mediums. For example, the upper jacket 715 may receive a thermal medium such as hot oil that is at a temperature greater than the thermal medium that received into the lower jacket 714. In some embodiments, a single jacket may be used.

The pay material may be fed into the evaporation chamber 720 and distributed along the heated surface 722 within the evaporation chamber 720. The short-path distillation unit 700 may include or be configured to operatively couple to a motor for rotating a rotor from which a plurality of wipers extend to contact and agitate pay material distributed along the heated surface 722 within the evaporation chamber 720. The short-path distillation unit 700 may also include or operatively couple to a vacuum pump 724 for evacuating atmosphere to thereby reduce pressure within the evaporation chamber 720. For example, the vacuum pump 724 may generate a low-pressure environment within the evaporation chamber 720, such as less than approximately −5 psi, less than approximately −10 psi, or lower. Exposure to the heated surface 722, agitation, and the low-pressure environment may result in selective evaporation of solvent and pay material components. Heavier components of the pay material flow to one or more pay ports 712 for collection and transport through one or more transport components comprising one or more transport lines 26a. Transport line 26a transports pay material to appropriate pay material storage tanks 43 or vessels as needed. For example, the pay material may be transported to one or more pay material storage tanks 43, which may include multiple pay material storage tanks 43 for collecting particular pay material components or blends of pay material components, which may include cannabinoid isolates by weight that pass through the short-path distillation unit 700. As described in more detail below and elsewhere herein, the short-path distillation unit 700 may be configured with a recirculating loop for refining multiple passes. For example, the short-path distillation unit 700 may be configured with a recirculating loop comprising transport lines 26a, 24b to recirculate the pay material that does not evaporate and passes through the short-path distillation unit 700. The recirculation loop may or may not include a pay material storage tank 43. As also described in more detail below and elsewhere herein, the extraction system 10 may include multiple short-path distillation units 700 and one or more condensers 800 comprising one or more distillation paths for isolating specific cannabinoids from the pay material by weight. In various embodiments, one or more pay product storage tanks 43 may be coupled by coupling line 23. Coupling line 23 may enhance scalability of the extraction system 10 by expanding the amount of pay product that can be stored between circulation runs or passes through the same or other short-path distillation units.

The vapor generated within the evaporation chamber 720 flows out of the short-path distillation unit 700 through the vapor port 732 and is flowed along line 28a to condenser unit 801. In various embodiments, the vapor may comprise gas and/or aerosol components.

Figure 9:
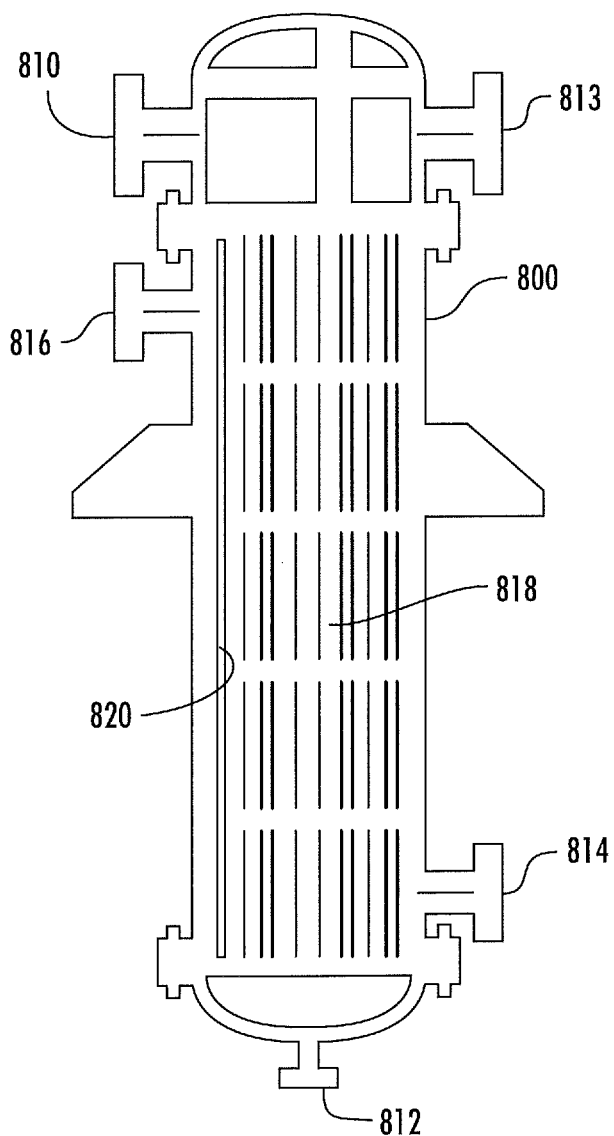
FIG. 9 illustrates a condenser unit of the extraction system according to various embodiments described herein.

With continued reference to FIG. 2 and further reference to FIG. 9, illustrating a cross-section of condenser unit 801 according to various embodiments, condenser unit 800 may include a vertical condenser 800. The condenser 800 may include an input port 810 for receiving vapor from line 26a and delivering the vapor into an interior flow path 818 of the condenser. The condenser 800 may be located proximate to the short-path distillation unit 700. In various embodiments, condenser unit 801 comprises a vertical condenser 800.

The condenser unit 801 may include a thermal component for cooling a surface within the interior volume 818. In the illustrated embodiment, the thermal component comprises a jacket 820 through which a thermal medium may be flowed. The thermal medium may include a cooling fluid. The supply of thermal medium may be the same or different than the supply used for other sub-process equipment and/or transport components. In the illustrated embodiment, the extraction system 10 includes or is configured to couple to a supply of a thermal material comprising cooling water, e.g., between 38° F. and −20° F.). The cooling water may be transported through thermal delivery line 38b and supplied into the jacket 818 through thermal delivery port 814. The cooling water may be flowed within the jacket 820 and discharged at thermal discharge port 816. The discharged water may them be transported along thermal return line 39b for cooling and recirculation or discharge.

The cooling water may cool a surface within the interior volume 818 onto which vapor may condense. The condenser 800 may be at low-pressure, such as less than approximately −5 psi, less than approximately −10 psi, or lower. The condenser 800 may separate remaining solvent and extracted pay material. The condensed solvent and pay material may be discharged at discharge port 812 positioned along a lower end of the condenser 800. Transport line 30a may define one or more fluid paths for receiving the condensate comprising separated solvent and one or more fluid paths for receiving condensate comprising separated pay material. Discharge port 812 may comprise multiple discharge ports coupled to transport lines 30a wherein the respective fluid paths may transport the condensates to various collection tanks 45. While only one collection tank is shown, collection tank 45 may include or couple to a solvent storage tank, which may be the same or a different tank than solvent storage tank 29. Collection tank 45 may also include one or more pay material collection tanks for collection or storage of one or more refined pay product components, such as various cannabinoids refined by weight. Collection tank 45, which can include solvent storage tanks, pay material storage tanks for further processing through the short-path distillation unit 700, or pay product collection tanks, may include coupling lines 29 for coupling multiple such collection tanks.

As introduced above and elsewhere herein, the extraction system 10 may be configured from multiple refining passes through multiple short-path distillation units 700 and one or more condensers 800. The short-path distillation units 700 and one or more condensers 800 may be aligned in parallel or in series and may define various distillation paths for separating various pay material components or combinations of pay material components by weight. In these or other embodiments, one or more short-path distillation units 700 may be configured for recirculation. For example, transport line 26a may recirculate pay material that does not evaporate within the short-path distillation unit 700 via return transport line 24b. Subsequent passes through one or more short-path distillation units 700 configured to evaporate higher weight components allows separation by weight an condensation of the evaporated components and either further separation of the condensate from the condenser 800 or transport to one or more pay product collection tanks, identified in FIG. 2 as collection tank 45, which may also include separate solvent tanks for solvent evaporated and condensed at lower temperatures.

Condenser unit 801 may also include a bypass port for discharge of residuals, e.g., gas, vapors, and/or aerosols that do not condense within the condenser 800. These vapors may be transported through line 30b and 30a to a pump 60 and a vapor-liquid separator 70 for recovery. In some embodiments, the pump 60 comprises a water ring pump. Pump 60 or another pump may be coupled to pay material storage tank 22b via a transport line 37 to collect gas, vapor, and/or aerosols within the pay material storage tank 22b and transport them to the vapor-liquid separator 70. The residual recovery and/or recovery from the pay material storage tank 22b will typically include terpenes and flavonoids which may be collected for analysis, addition to collected pay product, further isolated, or any combination thereof. The control system 1000 (see FIGS. 12 & 13) may allow the user, e.g., via the user interface 1050, to selectively initiate the pump 60 to pull through transport line 37. For example, the controller 1010 may open a valve along transport line 37 to allow the pump 60 to fluidically couple with the pay material storage tank 22b. In some embodiments, an operation program will specify timing of the controller 1010 initiating the pump 60 and/or fluidic coupling of the pump 60 and the pay material storage tank 22b. Transport line 37 may provide a further option for additional control over the extraction process. In some embodiments, the extraction system 10 may not include residual recovery processing.

As introduced above, one or more of the transport components may also comprise thermal components for providing temperature control to transported processing materials. For example, transport lines for transporting pay materials may include jackets for providing heat or cooling to the pay materials. In one example, thermal medium comprising hot water or oil is flowed through one or more transport lines that transport pay materials. In some embodiments, pay material or pay material storage tanks may be jacketed for receiving thermal medium in a similar manner to provide temperature control during storage.

The sub-process equipment and/or transport lines are preferably constructed from food grade stainless steel; however, other rigid construction materials may be used. The extraction system 10 may combine ultrasonic extraction and distillation performed at low-pressure with the use food grade solvents, and/or inline winterization. Crude pay material may be preheated prior to being fed into a wiped film evaporator at low-pressure for refining distillation and extraction of cannabinoids. In various embodiments, the entire apparatus is temperature controlled from end-to-end and incorporates hot steam/oil or chilled jacketed vessels and piping. Unlike $CO_2$ extraction that operates at high pressure, the extraction system 10 and process may operates at a low-pressure relative to the high pressures required for $CO_2$ extraction, which may include vacuum or negative atmosphere pressures as described herein. In various embodiments, one or more sub-process equipment and/or transport lines may include visualization portions and/or analysis portions to visualize and/or analyze pay material or other process materials. For example, as introduced above, a visualization portion 17 comprising a sight glass may be provided along the transport line 18a to visualize condensed pay material being transported from the condenser 300. In this or another embodiment, visualization and/or analysis portions may be provided on one or more of the solvent storage tank 29, extraction vessel 200, condenser 300, pay material storage tank 18b, winterization unit 400, filter unit 500, pay material storage tank 22b, preheater 600, short-path distillation unit 700, pay material storage tank 43, condenser 800, collection tank 45, or one or more of transport lines 14a, 16a, 18d, 20a, 20c, 22a, 22c, 24a, 24b, 26a, 28a, 30a, 30b, 30c, 37.

As introduced above, the extraction system 10 may be scalable. For example, vessels such as the solvent storage tank 29, extraction vessel 200, pay material storage tank 18b, pay material storage tank 22b, or collection tank 45 may be sized between 150 L and 6,000 L or more. Smaller sizes may also be used. In some examples, vessel may be further coupled thereby further increasing capacities of the extraction system 10. In various embodiments, the control system 1000 may be configurable to control system operations 1115 for various sized and combination of sized sub-process equipment and/or tanks. For example, a user, via the user interface 1050, may specify vessel sizes or capacities of the above or other sub-process equipment such as condenser 300, winterization unit 400, filter unit 500, condenser 800, or one or more of transport lines 14a, 16a, 18d, 20a, 20c, 22a, 22c, 24a, 24b, 26a, 28a, 30a, 30b, 30c, 37. The control program may then modify protocols of extraction programs or identify or select suitable extraction programs to be used. In various embodiments, a cannabis oil extraction method comprising utilizing the extraction system 10, as described herein, to extract cannabis oil and generate a refined pay product.

Figure 10:
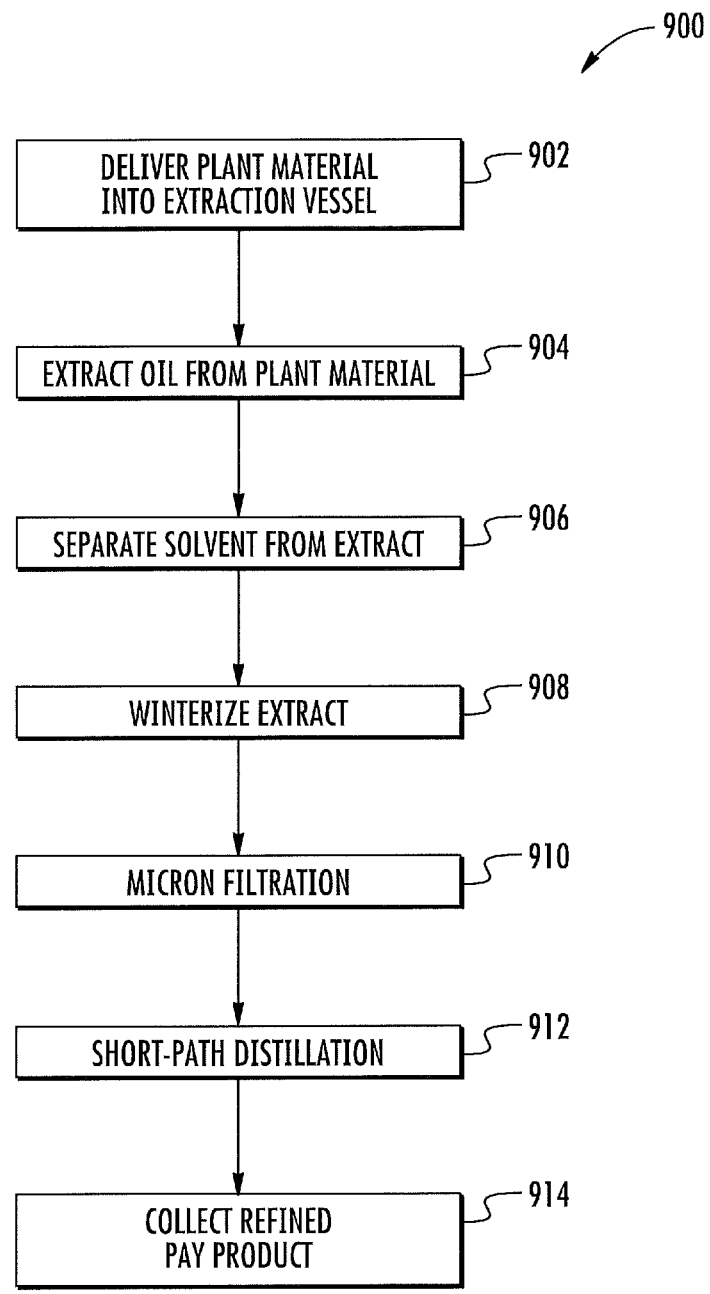
FIG. 10 is a method of extraction using an extraction system according to various embodiments described herein.

FIG. 10 illustrates a cannabis oil extraction method 900 according to various embodiments. The method 900 includes delivering plant material into an extraction vessel 902, extracting oil from the plant material 904, separating solvent from the extract 906, winterizing the extract 908, subjecting the extract to micron filtration 910, distilling the extract using short-path distillation 912, and collecting the refined pay product 914.

In various embodiments, delivering plant material into an extraction vessel 902 may include delivering plant material cut into pieces less than 3 inches, such as between 1 to 2 inches into an interior volume of an extraction vessel. The extraction vessel and/or delivery of plant material and/or solvent into the extraction vessel may be similar to extraction vessel 200 as described above with respect to FIGS. 1-3. For example, the plant material may be delivered into the extraction vessel wet. The solvent may be a food grade solvent, which may be a blend of food grade solvents. Other solvents may also be used. In one embodiment, the solvent is preferably a food grade solvent and/or a solvent that naturally occurs in the cannabis extract. The solvent may be delivered from a solvent storage tank.

Extracting oil from the plant material 904 may be similar to that described above with respect to the extraction vessel 200 (FIGS. 1-3). For example, the extraction may include utilizing cellular disruption comprising solvent and agitation. The plant material and solvent mixture may be mechanically agitated by an agitator. The agitator may include a rotating agitation member positioned within a central portion of an interior volume of the extraction vessel housing the solvent and plant material. Alternatively or additionally, agitation may include cellular disruption including introduction of soundwaves into the solvent. The extraction vessel may include one or more transducers configured to produce sonic and/or ultrasonic, soundwaves, e.g., between approximately 5 kHz and approximately 250 kHz or more. One or more transducers may comprise a full frequency transducer. The extraction may include rotating frequencies. In one example, the method 900 includes moving one or more movable transducers to better position the direct of soundwave emissions through the solvent.

Separating solvent from the extract 906 may be similar to that described above with respect to evaporation of solvent and extract from the extraction vessel and condensation of the steam and vapor with condenser 300 (FIGS. 1-4).

In any of the above or another embodiment, separating solvent from the extract 906 may include supplying heat to the extraction vessel. Supplying heat to the extraction vessel may include supplying a thermal medium comprising a hot fluid such as oil, water, gas, or steam to heat walls of the extraction vessel defining an interior volume wherein the extract and solvent mixture resides. The extraction vessel may be jacketed and define passages, such as paths or lines, through which the thermal fluid may flow. The passages may be adjacent to the interior volume, e.g., passages and the interior volume may be separated by a wall defining the interior volume. The thermal medium may provide heat to the extraction vessel up to approximately 220° F. Higher temperatures may be used by may result is cannabinoid degradation. Separating the extract 906 may also include evacuating atmosphere from the interior volume of the extraction vessel to generate a negative pressure environment. The pressure may be near vacuum. In one embodiment, the pressure is less than approximately −5 psi, less than approximately −8 psi, approximately −10 psi, or less than approximately −10 psi. The pressure may reduce a temperature at which components are subject to evaporation or boiling to promote evaporation or vaporization at lower temperatures. In one example, the thermal medium may provide heat to the extraction vessel up to approximately 210° F., approximately 200° F., or approximately 190° F., or lower.

In any of the above or another embodiment, separating solvent from the extract 906 may include selectively condensing the gas and steam to separate solvent from the extract. The method 900 may include feeding the gas and steam into a condenser. In one embodiment, the condenser is a horizontal condenser. The method 900 may include supplying a thermal medium comprising a chilled fluid to the condenser to cool one or more condensing surfaces. In one example, the condenser includes a jacket comprising passages for thermal medium to flow. The passages may be adjacent to or run behind condensing surfaces, for example. In one embodiment, separating solvent from the extract 906 further includes evacuating atmosphere from an interior flow path of the condenser to generate a negative pressure environment. The negative pressure environment may be near vacuum. In some examples, the negative pressure environment is less than approximately −5 psi, less than approximately −8 psi, approximately −10 psi, or less than approximately −10 psi. In one example, the negative pressure environment is approximately the same as a negative pressure environment within the interior volume of the extraction vessel. The method 900 may include evacuating the extraction vessel, condenser, or both with a pump. A same or different pump may be used. The method 900 may include flowing the gas and steam along an interior path defined by the condensing surfaces of the condenser to condense and thereafter recapture solvent that condenses on a portion of the condensing surface. The recaptures solvent may be transported to a solvent storage tank for reuse in future extractions. The method 900 may also include collecting low weight terpene condensate that condenses on a portion of the surface that is warmer than the surface onto which the solvent condenses. The collected terpene condensate may be transported to a terpene storage tank for reuse, e.g., recombining with refined cannabis oil pay product. The method 900 may also include collecting extract that condenses on a portion of the condensing surface that is cooler than the condensing surface onto which the solvent condenses. The condensed extract may be transported to for winterization. In one embodiment, condensed extract may be transported to and pay material storage tank before transporting the extract for winterization.

Winterizing the extract 908 may be similar to that described above with respect to winterization unit 400 (FIGS. 1, 2, & 5). For example, winterization may include an inline winterization process. Winterization may include flowing the pay material (extract) through and interior flow path of an inline winterization apparatus. The interior flow path may be defined by walls chilled to approximately −20° F. or below, such as between approximately −20° F. and approximately −50° F., such as less than −50° F. or less than −60° F. The method 900 may include reducing the temperature of the pay material to between approximately −20° F. and approximately −50° F. or less. The chilled pay material may be passing through a plurality of filters, which may be referred to a screens or size exclusion filters, to remove agglomerated fats, glycerin, and waxes. The winterized pay product may be transported to a micron filter for the next step.

Micron filtration 910 may be similar to that described above with respect to filter unit 500 (FIGS. 1, 2, & 6). For example, the micron filter may comprise a press filter or VSEP filter unit and the method 900 may include processing the pay material through the press filter or VSEP filter unit to filter particulates to the micron scale from the pay material.

The pay material may be transported from the micron filtration step to the short path distillation step 912. In some embodiments, a micron filtration step is not included or may be optional. In any of the above or another embodiment, the pay material may be transported to a preheater prior to being transported to the short-path distillation step 912. For example, the pay material may be preheated with a preheater in a manner similar to that described above with respect to preheater 600 (FIGS. 1, 2, & 7). In any of the above or another embodiment, the pay material may be transported to a pay material storage tank after being winterized or micron filtered, which may be before being transported to a preheater.

The short-path distillation 912 may be used to separate extract components and obtain refined pay products. In some embodiments, short-path distillation 912 comprises molecular distillation. Short-path distillation 912 of the pay material may be similar to that described above with respect to short-path distillation unit 700 and condenser 800 (FIGS. 1, 2, 8, & 9). For example, short-path distillation 912 may include using a wiped film, agitated, fallen, or thin film evaporation process.

The short-path distillation 912 may include supplying heat to an evaporation chamber, which may include multiple evaporation chambers. Supplying heat may include supplying a thermal medium comprising a hot fluid such as oil, water, gas, or steam to heat walls of an evaporation chamber. The evaporation chamber may comprise an interior volume of a film evaporator as described herein. The evaporation chamber may be jacketed to receive the thermal medium within passages of the jacket which may be adjacent to or underlying surfaces to heat. In one embodiment, multiple thermal mediums may be supplied to providing differential degree of heating. For example, higher heat medium may be provided to a jacket portion positioned to heat an upper portion of the evaporation chamber and lower heat medium may be provided to a jacket portion positioned to heat a lower portion of the evaporation chamber. The short-path distillation 912 may include evacuating atmosphere from the evaporation chamber to generate a negative pressure environment. The negative pressure environment may be near vacuum. In some examples, the negative pressure environment is less than approximately −5 psi, less than approximately −8 psi, approximately −10 psi, or less than approximately −10 psi.

The short-path distillation 912 may include feeding the pay material into the evaporation chamber. In some embodiments, the pay material may be distributed along a heated surface within the evaporation chamber and thereon agitated with a blade of wiper. The wiper may be a rotating wiper, for example.

Pay product that passes through the evaporation chamber may be recirculated for additional passes through one or more short-path distillation processes, which may be provided by one or more additional short-path distillation units, having different parameters to target particular pay material components, e.g., by weight. In one embodiments, the pay material that passes through the evaporation chamber may be stored in a pay material recirculation storage tank prior being recirculated. In one embodiment, pay material passing through the evaporation chamber is collected as refined pay product.

Vapor, which may include gas and aerosols, produced in the evaporation chamber may be transported to a condenser, which may include multiple condensers. The condenser may be similar to condenser 800 described above with respect to FIGS. 1, 2 & 9. The short-path distillation 912 may include supplying a thermal medium to the condenser to cool the condenser. The thermal medium may comprise a cool fluid such as water or gas that may be used to cool walls or surfaces of an interior passage of the condenser. In one embodiment, the condenser is jacketed to receive the thermal medium within passages of the jacket which may be adjacent to or underlying surfaces to cool. The short-path distillation 912 may include evacuating atmosphere, e.g., with a pump, from the interior passage to generate a negative pressure environment. The negative pressure environment may be near vacuum. In some examples, the negative pressure environment is less than approximately −5 psi, less than approximately −8 psi, approximately −10 psi, or less than approximately −10 psi.

The method 900 may further include flowing the vapor generated from the evaporation chamber through the interior passage of the condenser and collecting condensate. The may include residual solvent and thus the method 900 may include recapturing residual solvent that condenses on a portion of the condensing surface. The residual solvent collected as condensate from the condenser may be transported to a solvent storage tank.

The method 900 may also include flowing residual vapor to a vapor-liquid separator to separate remaining low weight extract components such as terpenes and flavonoids.

Condensate collected from the condenser may include pay material. This pay material may be collected and kept as refined pay product at step 914 or may be sent back for additional separation of the pay materials. In some embodiments, this may include an intermediate transport to a recirculation pay material storage tank before being recirculated for additional passes through one or more short-path distillation processes, which may be provided by one or more additional short-path distillation units, having different parameters to target particular pay material components, e.g., by weight. For example, the method 900 may include repeating molecular distillation of condensed pay material and/or non-evaporated pay material at increased temperature in the evaporation chamber to obtain further refined pay product by weight.

To counter thermal loss during residence time in a pay material recirculation tank or time of transport, pay material, such as condensate or pay material passing through the evaporation chamber may also be recirculated through the preheater prior to recirculation through the evaporation chamber. In some embodiments, a valve may be used to route the pay material along transport lines for recirculation through the preheater or to bypass the preheater before recirculation through the evaporation chamber. As introduced above, the preheater may heat the pay material for to a desired temperature for the particular weight separation desired during circulation or recirculation through the evaporation chamber.

In further embodiments, method 900 may also include adding terpenes and/or flavonoids recaptured following during the separation of solvent from extract step 906 to the collected refined pay product. In this or another embodiment, the method 900 may include adding terpenes and/or flavonoids recaptured during the short-path distillation step 912 to the collected refined pay product.

In various embodiments, method 900 may be performed utilizing an end-to-end processing apparatus, such as extraction system 10 described above (FIGS. 1-9) and elsewhere herein.

Figure 11:
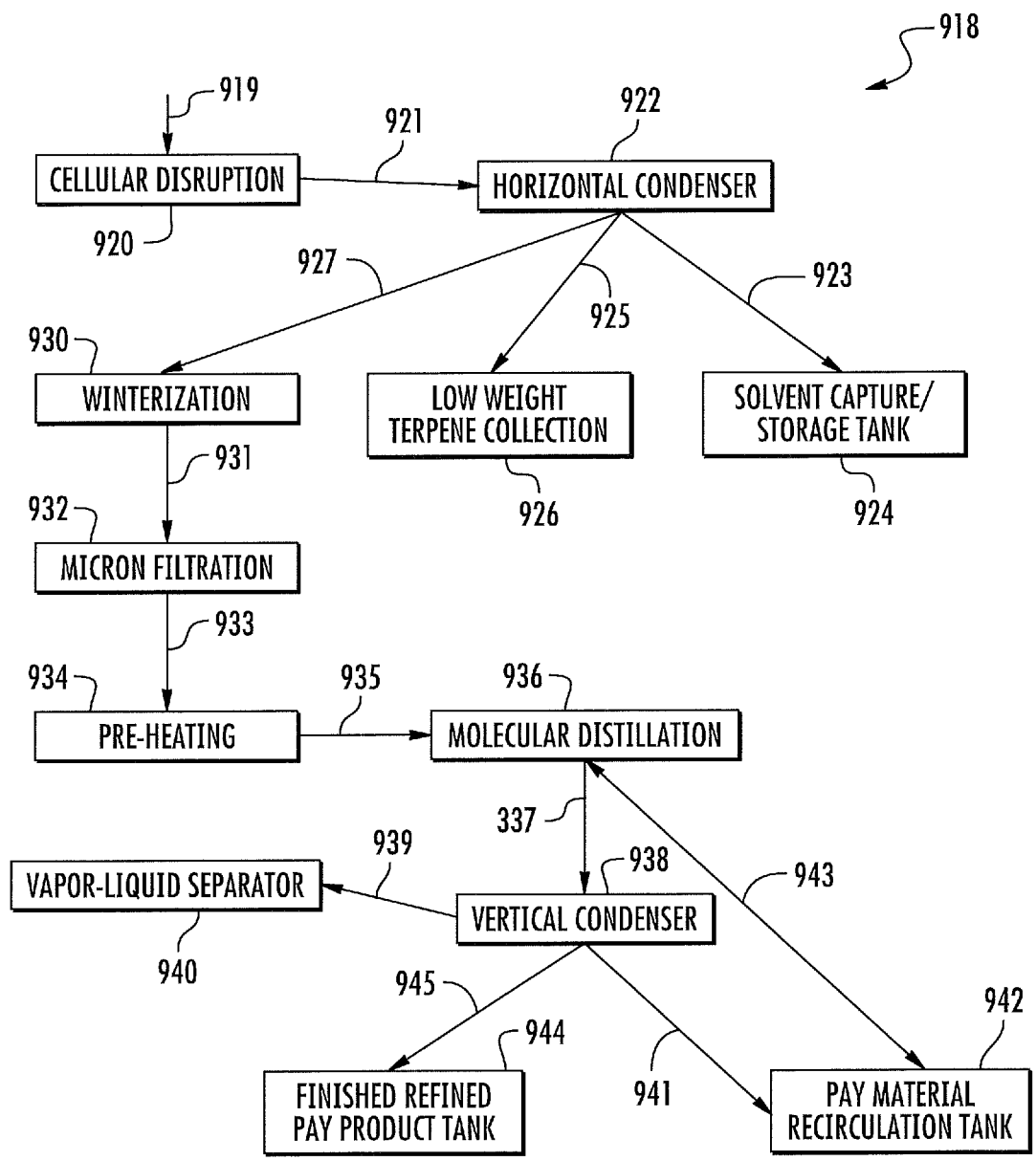
FIG. 11 is a method of extraction using an extraction system according to various embodiments described herein.

FIG. 11 illustrates another embodiment of a cannabis oil extraction method 918. The method 918 may be similar to the method 300 described with respect to FIG. 10. Plant material 919 may be input into the process and subjected to cellular disruption 920 to extract cannabis oil from the plant material. The cellular disruption 920 may be performed in an extraction vessel as described herein with respect to extraction vessel 200 (FIGS. 1-3) and with respect to step 904 of method 900 (FIG. 10). For example, the cellular disruption 920, e.g., via mechanical agitation and/or sonic agitation, may release the pay material into a surrounding solvent. Low-pressure and heat may be applied such that solvent and extract vaporize or evaporate into gas and steam 921.

The gas and steam 921 may be subsequently condensed in a horizontal condenser 922. Condensing the solvent and extract in the horizontal condenser 922 may be similar to that described herein with respect condenser 300 (FIGS. 1, 2, & 4) and with respect to the condensation aspects of the separating the solvent from the extract step 906 of method 900 (FIG. 10). The horizontal condenser 922 may condense the solvent portion of the steam and gas to wherein the condensed solvent 923 may be transported to a solvent capture or solvent storage tank 924. The horizontal condenser 922 may also condense a portion of the extract comprising low weight terpenes 925, which may be collected 926 for later use. The horizontal condenser 922 may also condense the remaining portion of the extract 924.

The extract 924 may next be subjected to winterization 930. Winterization may be similar to that described above with respect to winterization unit 400 (FIGS. 1, 2, & 5) and the winterization step 908 of method 900 (FIG. 10).

The winterized extract 931 may subjected to micron filtration 932 to remove particulates to the micron scale. Micron filtration 932 may be similar to that described above with respect filtration unit 500 (FIGS. 1, 2, & 6) and the micron filtration step 910 of method 900 (FIG. 10).

The micron filtered extract 933 may be preheated at step 934 prior to the preheated extract 935 being subjected to molecular distillation 936. Preheating may be similar to that described above with respect to with respect preheater 600 (FIGS. 1, 2, & 7).

The molecular distillation 936 may be similar to the process described with respect to the short-path distillation unit 700 (FIGS. 1, 2, & 8) and the short-path distillation described with respect to the short-path distillation step 912 of method 900 (FIG. 10).

The molecular distillation 936 evaporates a portion of the extract. This vapor 337, which may include gas and aerosol, may be condensed in a vertical condenser 938.

A portion of the vapor 337 at initial evaporation stages or molecular distillations at lower temperatures may include residual solvents, which may be condensed in the vertical condenser 938, collected, and sent to a solvent tank for reuse or disposal.

A portion 939 of the vapor 337 may fail to condense in the vertical condenser 938 and may be transferred to a vapor-liquid separator 940. The vapor-liquid separator 940 and the related processing may be similar to that described above with respect to the vapor-liquid separator 70 (FIG. 2) and with respect to method 900 (FIG. 10).

Condensed pay product 945 may be collected and stored in a finished refined pay product storage tank 944. Vapor 337 that condenses in the vertical condenser 938 may include pay material 941 that may be sent to a pay material recirculation tank 942, e.g., if further separation of components within the pay material is desired. Additionally or alternatively the pay material recirculation tank 942 may receive pay material 943 that fails to evaporate during molecular distillation 936. This pay material 941, 943 may be recirculated for further molecular distillation 936. The recirculation may be similar to that described above with respect to FIGS. 1, 2, 8, & 9 and method 900 (FIG. 10). For example, multiple passes through one or more distillation and condensers may be utilized to achieve a desired weight separation of pay product components. The vapor 337 generated from the molecular distillation 936 of the recirculated pay material 941, 942 may be sent to the vertical condenser 938 where the resulting condensate of the pay product 945 having the desired weight separation may be collected in the finished refined pay product tank 944, which may be similar to the pay product collection tank described above with respect to FIG. 2 and method 900 (FIG. 10).

In various embodiments, method 900 may be performed utilizing an end-to-end processing apparatus, such as extraction system 10 described above (FIGS. 1-9) and elsewhere herein.

In some embodiments, solvent may be added to the extraction vessel 200 prior to the plant material. Plant material may also be added before or during addition of solvent. In one embodiment, the solvent may be delivered into the interior volume preheated.

In various embodiments, the extraction vessel 200 or another extraction vessel may be fed a crude extract extracted by the extraction unit 201 or another extraction apparatus for extracting plant material utilizing modified, additional, or other extraction methodologies than those described above with respect to FIGS. 1-3, 10, & 11 and elsewhere herein. For example, the extraction system 10 may comprise an extraction unit 201 configured for an extraction process utilizing additional or other extraction methodologies in addition to or instead of mechanical agitation in solvent, sonication in solvent, and/or mechanical agitation in solvent together with sonication. In one embodiment, the extraction vessel 200 may contain or be fed a solvent/extract mixture generated from another extraction process. The extraction vessel 200 may heat the solvent/extract mixture to generate a gas, preferably vapor, for subsequent separation by the condenser unit 310 (see, e.g., FIGS. 1, 2 & 4) or another condenser apparatus. In one example, the extraction vessel 200 may also provide a low-pressure environment in addition to an elevated temperature environment. In a further or another example, the extraction vessel 200 may be configured to agitate the solvent/extract material using mechanical agitator 210 to promote transition of the mixture into gas components, which may include vapor, steam, and/or aerosol components. As introduced above, providing a low-pressure environment reduces boiling points required for vaporization and reduces cannabinoid burn off and degradation. In one embodiment, the condenser unit 310 (see, e.g., FIGS. 1, 2 & 4) may be fed a solvent/extract gas mixture generated from another extraction unit and/or extraction process. In one embodiment, the winterization unit 400 may be fed a crude extract obtained from another extraction unit, extraction process, condenser unit, or solvent separation process. In any of the above embodiments, subsequent processing may be performed to further purify and/or separate extract components as described herein.

In various embodiments, an extraction system includes an extraction unit comprising a grinding assisted extraction vessel configured to perform an extraction process comprising grinding assisted extraction in solvent. In a further embodiment, the extraction system includes a co-solvent extraction vessel. For example, following grinding assisted extraction, a co-solvent extraction may be performed in the co-solvent extraction vessel with respect to all or a portion of the extract process materials evolving from the grinding assisted extraction in solvent. In a further embodiment, the extraction system includes a centrifuge vessel configured to separate extract process materials by centrifugation. In one example, following co-solvent extraction, ground plant material, solvent, and co-solvent may be fed into the centrifuge vessel for centrifugation. Centrifugation drives separation of solid plant material from extraction process liquids comprising extracted material, e.g., oils, solvent, and/or co-solvent. In one embodiment, all or a portion, e.g., a majority, of the co-solvent may be separated from the extracted material and solvent during the centrifugation process. Following centrifugation, the supernatant may be subjected to further separation steps. For example, the supernatant may include water from performing the extraction process using wet plant material. The centrifugation may result in division of oil and water phases in the supernatant, which may then be separated manually or via automation machinery. The supernatant, comprising the oil phase or both the oil and water phases, may be heated to drive evaporation or vaporization. Evaporation or vaporization may generate a gas, which may include vapor and/or aerosol. In some embodiments, the supernatant may also be heated while held at a vacuum pressure to drive evaporation or vaporization. The gas may subsequently be fed into a condenser, such as condenser 301 unit (see, e.g., FIG. 1), for further separation of solvent, co-solvent, and/or extraction material components. Subsequent processing may also be performed to further purify and/or separate extract components as described herein. In one embodiment, the extraction vessel does not include a sonication transducer, agitator, or both. In one embodiment, the extraction vessel includes pressure and heat control components to generate vapor includes generating a low-pressure environment, such as a below atmosphere or vacuum pressure as described herein. In some embodiments, additional processing steps and/or apparatuses may be used in addition to or instead of the above described vessels and processes. For example, prior to co-solvent extraction in the co-solvent extraction vessel, ground plant material and solvent may be chilled in a chiller vessel. The chiller vessel may comprise the same or a different vessel than vessels in which solvent and/or co-solvent extraction are performed. In a further or another example, the extraction unit includes a solvent mixing vessel within which solvent is mixed with plant material prior to grinding assisted extraction. The mixing vessel may include a mixer, e.g., a stirrer or agitator. In one embodiment, the grinding assisted extraction vessel includes a vessel in which both mixing and grinding assisted extraction are performed. Thus, it will be appreciated that the extraction unit may comprise an extraction vessel comprising one or more extraction vessels, e.g., mixing vessel, grinding assisted extraction vessel, chiller vessel, co-solvent extraction vessel, centrifugation vessel, evaporation or vaporization vessel, or combination thereof. Combinations of the one or more extraction vessels may be embodied in a same vessel. In some embodiments, any of the one or more extraction vessels comprises a plurality of vessels.

FIG. 14 illustrates an extraction method 1100 according to various embodiments. The extraction method 1100 may include grinding assisted extraction in solvent 1102, co-solvent extraction 1104, and centrifugation 1106. In a further embodiment, shown, the extraction method may include evaporation 1108. In still further embodiments, the extraction method may comprise one or more of winterization, dewaxing, distillation, or other separation and/or purification techniques. In some embodiments, the extraction method 1100 may be used in a full spectrum extraction.

Grinding assisted extraction in solvent 1102 may include grinding plant material while in intimate contact with solvent. In some implementations, the extraction method 1100 may also include supplying plant material into an extraction vessel including a grinder configured to grind the plant material. A solvent may be provided into the extraction vessel and therein be in intimate contact with the plant material while the grinder grinds the plant material. In some embodiments, the plant material may be preprocessed as described above and elsewhere herein. In one example, the extraction method 1100 further includes preprocessing the plant material by grinding the plant material to small pieces, e.g., into pieces having a largest dimension of approximately 1 to approximately 2 inches or less. Other size pieces may be used, such as larger pieces having a largest dimension less than approximately 5 inches or less than approximately 3 inches or smaller pieces having a largest dimension less than 1 inch or less than half an inch, for example. Larger pieces may also be used but may reduce yield and/or increase extraction time and overall process efficiency. In one embodiment, the plant material is preprocessed into pieces having average dimensions of between approximately 800 microns to approximately 1400 microns.

In various embodiments, the solvent comprises one or more nonpolar solvents. Nonpolar solvents for grinding assisted extraction in solvent 1102 may include a nonpolar solvent selected from pentane, hexane, benzene, toluene, carbon tetrachloride, benzene, glycerol monooleate, diethyl ether, hexane, methylene chloride, carbon dioxide, methane, ethylene, or combination thereof. In one embodiment, the solvent comprises one or more nonpolar solvents selected from D-limonene, olive oil, soybean oil, coconut oil, medium chain triglycerides, methanol, ethanol, propylene glycol, polysorbates 20 and 80 (tween 20 and 80), poloxamer 188. Other nonpolar solvents may be used instead or additionally, such as nonpolar solvents classified as food grade by the Federal Drug Administration. In one method, the solvent comprises a single nonpolar solvent, such as glycerol monooleate. In some embodiments, the solvent includes a somewhat nonpolar solvent such as chloroform, diethyl ether, or deuterated chloroform (heavy chloroform for NMR), for example. In one embodiment, the nonpolar solvent comprises glycerol monooleate.

In an above or another embodiment, the solvent comprises a polar solvent or a solvent of intermediate polarity. In some embodiments, additional or other solvents may be used. For example, a solvent of intermediate polarity such as polyethylene glycol, tetrahydrofuran, ethyl acetate, or dichloromethane may be used in addition to or instead of a nonpolar solvent. In these or other embodiments, a polar solvent may be used in addition to or instead of a nonpolar or solvent of intermediate polarity such as water, deuterium oxide (heavy water for NMR), ethanol, methanol, acetone, methyl ethyl ketone, isopropanol, n-propanol, acetonitrile, DMSO (dimethyl sulfoxide) or deuterated DMSO (heavy DMSO for NMR), or DMF (dimethyl formamide).

The amount of solvent used in the grinding assisted extraction in solvent 1102 may vary, but will generally be between approximately a 2:1 and approximately a 4:1 ratio of solvent to plant material on a weight basis. It is to be appreciated that larger ratios of solvent to plant material may be used and may obtain more complete extraction; however, the present extraction methodology may also be utilized to obtain high quality extraction products with such lower ratios of solvent to plant material.

During grinding assisted extraction in solvent 1102, the plant material may be ground to micron and/or submicron particle sizes while in intimate contact with the solvent. An average particle size of solid plant material resulting from the grinding process may vary but may preferably be approximately 100 microns or less, or more preferably approximately 40 microns or less. It will be appreciated that micronization to particle sizes greater than approximately 100 microns may also be used, but may result in a less efficient extraction.

The temperature of the process materials, e.g., solvent and plant material, during grinding assisted extraction in solvent 1102 may preferably be brought to and/or maintained at approximately 80° C. or less, approximately 60° C. or less, approximately 50° C. or less, or more preferably approximately 40° C. or less, such as approximately 30° C. or less, or approximately 20° C. or less.

Grinding assisted extraction in solvent 1102 may be performed at atmospheric pressure, e.g., approximately 760 torr. However, in some embodiments, grinding assisted extraction in solvent 1102 is performed under vacuum. For example, during the grinding assisted extraction in solvent 1102, the processing environment may be held at a low vacuum (approximately 760 torr to approximately 25 torr), a medium vacuum (approximately 25 torr to approximately $10^{-3}$ torr), a high vacuum (approximately $10^{-3}$ to approximately $10^{-9}$ torr), an ultra high vacuum (approximately $10^{-9}$ to approximately $10^{-12}$ torr), an extremely high vacuum (positive pressure less than approximately $10^{-12}$ torr), or a perfect vacuum (0 torr). When performed under vacuum, vacuum pressure may cause expansion of the surface area of the material to allow for more homogeneous mixture/contact of solvent and material.

In various embodiments, the duration of grinding may be as quick as approximately 20 minutes to approximately 40 minutes, such as approximately 30 minutes. However, longer or shorter grinding durations may be utilized. The grinding process may generate extraction process material comprising a homogeneous mixture of ground plant material, plant material extract, and solvent.

Following grinding assisted extraction in solvent 1102, the method may include addition of co-solvent for co-solvent extraction 1104. One or more co-solvents may be added to the extract process material that includes a mixture of plant material, plant material extract, and solvent. The co-solvent may include a co-solvent having both polar and nonpolar components, such as liquid $CO_2$. The liquid $CO_2$ may act as a co-solvent and wash. While the co-solvent will generally be referred to herein as being liquid $CO_2$, such as subcritical liquid $CO_2$, in some embodiments, additional or other co-solvents may be used, such as co-solvents having both polar and nonpolar components. Co-solvent extraction 1104 with liquid $CO_2$ may also be referred to herein as subcritical liquid $CO_2$ extraction.

Prior to addition of the liquid $CO_2$ co-solvent, the extract process material may be subjected to a cooling phase to cool the mixture to approximately 30° C. or less, such as approximately 24° C. or less, or between approximately 24° C. and approximately 21° C., and/or between approximately 24° C. and approximately −18° C. prior to addition of liquid $CO_2$. In one embodiment, the extract process material may be held at between approximately 21° C. and approximately 24° C. for a period of time before addition of the $CO_2$ co-solvent. It will be appreciated that some methodologies may skip the cooling process and/or may include addition of one or more co-solvents during the cooling process. In some embodiments, temperature of the extract process materials generated during grinding assisted extraction in solvent 1102 is sufficiently low to maintain liquid $CO_2$ added during co-solvent extraction 1104 in a liquid phase at the pressure provided during co-solvent extraction 1104 and an additional chilling step is not required. When the co-solvent includes additional or other co-solvents and the extraction method 1100 includes a chilling step, some embodiments may add such co-solvents prior to, during, or after the chilling step.

As noted above, addition of co-solvent to the extract process material may comprise addition of liquid $CO_2$. Liquid $CO_2$ may be added to the extract process material at a ratio of approximately 4 parts liquid $CO_2$ to approximately 1 part extract process material to approximately 1 part liquid $CO_2$ to approximately 2 parts extract process material. For example, liquid $CO_2$ may be added to the extract process material at a ratio of approximately 3:1 or more preferably approximately 1:1, on a weight basis. The liquid $CO_2$ may be maintained in a subcritical liquid phase during co-solvent extraction 1104 via maintenance of a suitable pressure and temperature combination during extraction.

To maintain the $CO_2$ in a liquid phase, the ground plant material, plant extract, solvent, and co-solvent mixture may be maintained at a low-pressure, relative to the high pressures required for supercritical $CO_2$ extraction, and a low temperature during co-solvent extraction 1102. Carbon dioxide has a critical point of approximately 31.1° C., 73.9 bar ($5.44 \times 10^4$ torr). At higher temperatures and equivalent or higher pressures, $CO_2$ acts as a supercritical fluid. At lower temperatures to approximately −56.4° C., $CO_2$ may exist as a gas or a liquid depending on pressure. Phase diagrams and transition points for $CO_2$ are known. In various embodiments, to keep $CO_2$ in a liquid state, a temperature range between −54° C. and 30° C. and pressure greater than approximately 5.1 bar ($3.88 \times 10^3$ torr) and less than approximately 72 bar ($5.4 \times 10^4$ torr) respectively may be used. For example, the extract process material may be maintained at approximately 30° C. or less, such as approximately 24° C. or less, between approximately 24° C. and approximately 21° C., or between approximately 24° C. and approximately −18° C. in combination with a suitable pressure to maintain the $CO_2$ in liquid phase. In one embodiment, the extract process material may be maintained at approximately 21° C. For increased safety, the pressure is preferably less than approximately 60 bar, less than approximately 50 bar, less than approximately 40 bar, or less than approximately 30 bar. More preferably, the pressure is less than approximately 20 bar, less than approximately 10 bar, less than approximately 8 bar, or less than approximately 6 bar, such as between approximately 5.2 bar and approximately 10 bar. In some embodiments, co-solvent extraction may including agitating the mixture during the co-solvent extraction with subcritical $CO_2$.

As noted above, the extract process material may be maintained at pressures that together with temperature combinations is suitable to maintain the $CO_2$ in liquid phase in which it acts as a supercritical fluid. Beneficially, as introduced above, the disclosed extraction process may be performed at lower pressures compared to the pressures required for supercritical $CO_2$ extraction techniques, thus, greatly improving safety. It will be appreciated that higher pressures suitable to maintain the $CO_2$ in the liquid phase may be used even if such pressures may also be used in combination with higher temperatures in supercritical extraction. The time provided for co-solvent extraction may vary and may be tuned to correspond to extraction process parameters.

In some embodiments, extraction with co-solvent may be performed for as few as approximately 20 minutes or less, such as approximately 10 minutes or less. In one example, extraction in co-solvent may be performed for between approximately 20 minutes and approximately 10 minutes. Longer co-solvent extraction processing times may also be used.

Following co-solvent extraction 1104, the extract process material may be separated to isolate solid plant material and liquid. Separation may also include separation of the liquid phase into oil and water phases, which may also be referred to as organic and aqueous phases. In the illustrated embodiment, separation is obtained by subjecting the extraction material to centrifugation 1106 in a centrifuge. During the centrifugation 1106, the extract process material may be separated based on specific gravity such that the solid ground plant material pellets and the supernatant contains the extract and solvent. The supernatant may also include residual water. Centrifugation 1106 may also drive phase separation of the supernatant, e.g., water phase and oil phases. For example, separation via centrifugation 1106 may result in a three-phase separation that includes solid, oil, and water phases.

In some embodiments, pressure and/or temperature may be controlled between co-solvent extraction 1104 and centrifugation 1106. In one example, the temperature of the extract process material may be increased actively or passively prior to introduction into the centrifuge or while resident in the centrifugation vessel. For example, the extract process material may be transferred to a holding vessel for a period of time to allow the temperature to normalize with the surrounding environment. In another example, the holding vessel may be heated, e.g., with a heating element or warm fluid flowed through a jacket. In one example, the temperature of the warming fluid may be greater than a desired temperature of the extract process material. In one example, the centrifuge comprises a holding vessel separate or together with a vessel used for the centrifugation process. In another example, the extract process material may be heated while in transit between co-solvent extraction 1104 and centrifugation 1106 steps. For instance, jacketed in-line pipping may be used wherein a heating fluid such as warm water may be flowed through the jacket. In one example, the heating fluid may be a temperature greater than 24° C., greater than approximately 27° C., greater than approximately 30° C., or greater than approximately 32° C., such as approximately 26° C., approximately 29° C., approximately 31° C., or approximately 32° C. In a further example, the extract process material may be at a temperature of approximately 21° C. after co-solvent extraction and may be heated to approximately 27° C. before centrifugation 1106.

In one embodiment, the extract process material may enter the centrifuge at approximately atmospheric pressure and atmospheric temperature. In some embodiments, temperature of the extract process material may be increased to greater than approximately 23° C., greater than approximately 25° C., greater than approximately 27° C., greater than approximately 29° C., or between approximately 23° C. and approximately 30° C., between approximately 24° C. and approximately 29° C., between approximately 24° C. and approximately 27° C., such as approximately 24° C., approximately 25° C., approximately 26° C., approximately 27° C., approximately 28° C., approximately 29° C., approximately 30° C., or approximately 31° C. prior to centrifugation 1106. Centrifugation 1106 may be accompanied by an increase in heat. For example, the centrifugation 1106 may result in moderate heating of the extract process material, such as a temperature rise of approximately 3° C., assisting in phase transition of the liquid $CO_2$ component. The temperature and pressure of the extract process material before or during centrifugation 1106 may be such that the moderate heating resulting from centrifugation 1106 is sufficient to transition the liquid $CO_2$ to gas phase, allowing the $CO_2$ to separate from the extract process material. Centrifugation 1106 may also assist in degassing the extract process material due to sheer force, similar to that of shaking up a can of soda. Temperatures above approximately 32° C. or 33° C. during centrifugation 1106 are typically sufficient to convert the liquid $CO_2$ into a gas.

Beneficially, the degassed $CO_2$ may be recovered for reuse. For example, a small vacuum may be applied to withdraw the $CO_2$ prior to centrifugation 1106, in the centrifuge vessel, or a subsequent vessel for $CO_2$ recovery. The $CO_2$ may then be subsequently separated from the supernatant by increase of temperature and/or reduction in pressure. The $CO_2$ gas may then be stored as gas or condensed as described above for reuse or disposal. However, centrifugation assisted degassing may be used to increase efficiency. In some embodiments, heat may be extracted from separated, e.g., degassed, $CO_2$ gas to condense the gas for liquid storage and/or reuse. For example, the $CO_2$ gas may be transported through a reduced temperature and/or increased pressure environment, which may include a condenser that extracts heat from the $CO_2$ gas.

Thus, the method 1100 may include separation, such as solid and liquid phase separation, that further combines specific co-solvent separation from the liquid phase within the solid and liquid phase separation process. For example, the temperature and pressure combination of the extract process material may be controlled such that a small rise in temperature accompanying centrifugation 1106 processing is sufficient to drive or assist in $CO_2$ liquid to gas transition.

In some embodiments, the extract process material may be given an initial degassing period in which the material is allowed to partially degas prior to centrifugation 1106, which may occur during active or passive heating, e.g., all or a portion of the extract process material may be actively heated to a temperature sufficient to drive degassing at the material pressure, such as a temperature above approximately 32° C. or approximately 33° C. at atmospheric pressure. In one embodiment, the extract process material may be allowed to substantially degas of $CO_2$ prior to centrifugation. In another embodiment, the extract process material is subjected to centrifugation 1106 at a reduced temperature approximately equivalent to that used for co-solvent extraction 1104 and thereafter allowed to further degas. In some embodiments, the extract process material may degas of $CO_2$ during transit between co-solvent extraction 1104 and centrifugation 1106, during centrifugation 1106, following centrifugation 1106, or combination thereof.

As noted above, the separation process may also include further separation of the liquid phase, e.g., by density, which will typically result in an oil phase and water phase separation. It will be appreciated that co-solvent may be separated utilizing other techniques before or after centrifugation 1106. For example, centrifugation 1106 may be performed under low temperature and/or low-pressure conditions sufficient to maintain the liquid state of the $CO_2$.

Centrifuge speeds during centrifugation 1106 may vary. In some examples, centrifuge speeds may range from approximately 9,000 rpm and approximately 12,000 rpm. Greater or lower speeds may be used. Greater speeds may increase temperature to a greater extent. Duration of centrifugation 1106 may vary. In some embodiments, durations may correspond to a processing rate of between approximately 9 gallons and approximately 30 gallons per minute.

As introduced above, centrifugation 1106 may separate the solid plant material from the plant extract and solvent, which are present in the supernatant. The co-solvent may be separated before centrifugation 1106, during centrifugation 1106, after centrifugation, or combination thereof. The solvent, such as a nonpolar solvent, may molecularly bond with extract compounds, thereby acting as a carrier fluid to pull the extract compounds from the solid plant material into the liquid medium during centrifugation 1106. When wet plant feed is used, the supernatant will generally include a less dense water phase in addition to the denser oil phase that represents residual moisture contained in the wet plant material feed. Thus, centrifugation 1106 may provide a three-phase separation of the extract process material at different specific gravities, e.g., solids, oils, and less dense water. The solids phase may be removed at this time. In some embodiments, the water phase may also be removed at this time. In some embodiments, the water phase may be processed to purify the water and collect extract components contained within the water. As noted above, centrifugation 1106 may result in transition of all or a portion of the $CO_2$ co-solvent to gas, allowing separation of the same. Thus, in some embodiments, centrifugation may also provide co-solvent separation. In one embodiment, the oil phase containing the plant extract and solvent may be allowed to expand, e.g., within an expansion tank, to allow further degassing following centrifugation 1106. Active or passive heat may be applied to accelerate expansion and degassing.

The supernatant including the crude plant extract may comprise a solvent/extract mixture including all or a portion of one or more of the solvents, which may include a portion of the co-solvent. The solvent/extract mixture may be processed as described above utilizing the relevant units of system 10 (FIGS. 1-9) and/or relevant steps of methods 900, 918 (FIGS. 10 & 11) or by one or more additional or other methodologies for separation of solvent from the extract oil. In one embodiment, centrifugation 1106 may be combined with or replaced by straining and/or pressing of the mixture to separate the extract and solvent from the solid plant material.

The extraction method 1100 may also include a solvent separation step 1108. For example, solvent separation 1108 may include transitioning one or both of the solvent, extract, or portions thereof of the solvent/extract mixture to a vapor phase. Solvent separation may include application of heat to the solvent/extract mixture. In some examples, heat may be accompanied by a low-pressure environment having a vacuum pressure. The vapor portion, which may include steam, may be condensed using a condenser. For example, controlled condensation of vapor comprising solvent may separate solvent from extract allowing the solvent to be reused. In some embodiments, all or a portion of the extract is not subject to evaporation. In various embodiments, evaporation, separation of solvent, condensation, isolation, and/or purification of one or more components of the extract from the solvent/extract mixture may utilize the relevant units of system 10 (FIGS. 1-9) and/or relevant steps of methods 900, 918 (FIGS. 10 & 11) described herein or by one or more additional or other methodologies. For example, solvent separation 1108 may include heating the solvent/extract mixture as described with respect to extraction unit 201 and thereafter transferring the vapor to condenser unit 301. In one example, the extraction unit 201 utilized for heating the solvent/extract mixture in the extraction vessel 200 prior to condensing does not include sonication transducer 220. Heating may be accompanied by a low-pressure environment, for example. In a further embodiment, the extraction unit 201 utilized for heating the solvent/extract mixture in the extraction vessel 200 prior to condensing also does not include an agitator 210. Thus, in some embodiments, the solvent/extract mixture obtained according to extraction method 1100 may be heated and subjected to a vacuum, e.g., near vacuum, as described with respect to extraction unit 201 to generate vapor prior to transfer to the condenser unit 301. Further processing through system 10 may be used to separate and recover desired plant components or whole plant extract. In some embodiments, the plant extract, when separated from the solvent and co-solvent, comprises a full-spectrum extract or whole cannabis plant extract.

Beneficially, various embodiments of the extraction method 1100 may be performed with wet plant feed thereby avoiding costly drying steps, which also damage and/or degrade available extract components. Indeed, utilization of wet plant feed may be preferred to dry plant feed in order to obtain extract representing a more complete spectrum of the available extract components present in fresh cut plant material. It will be appreciated that in some embodiments one or more steps of the extraction method 1100 may be excluded. For example, the extract/solvent mixture following centrifugation 1106 may be packaged for supply to another process or use.

Figure 15:
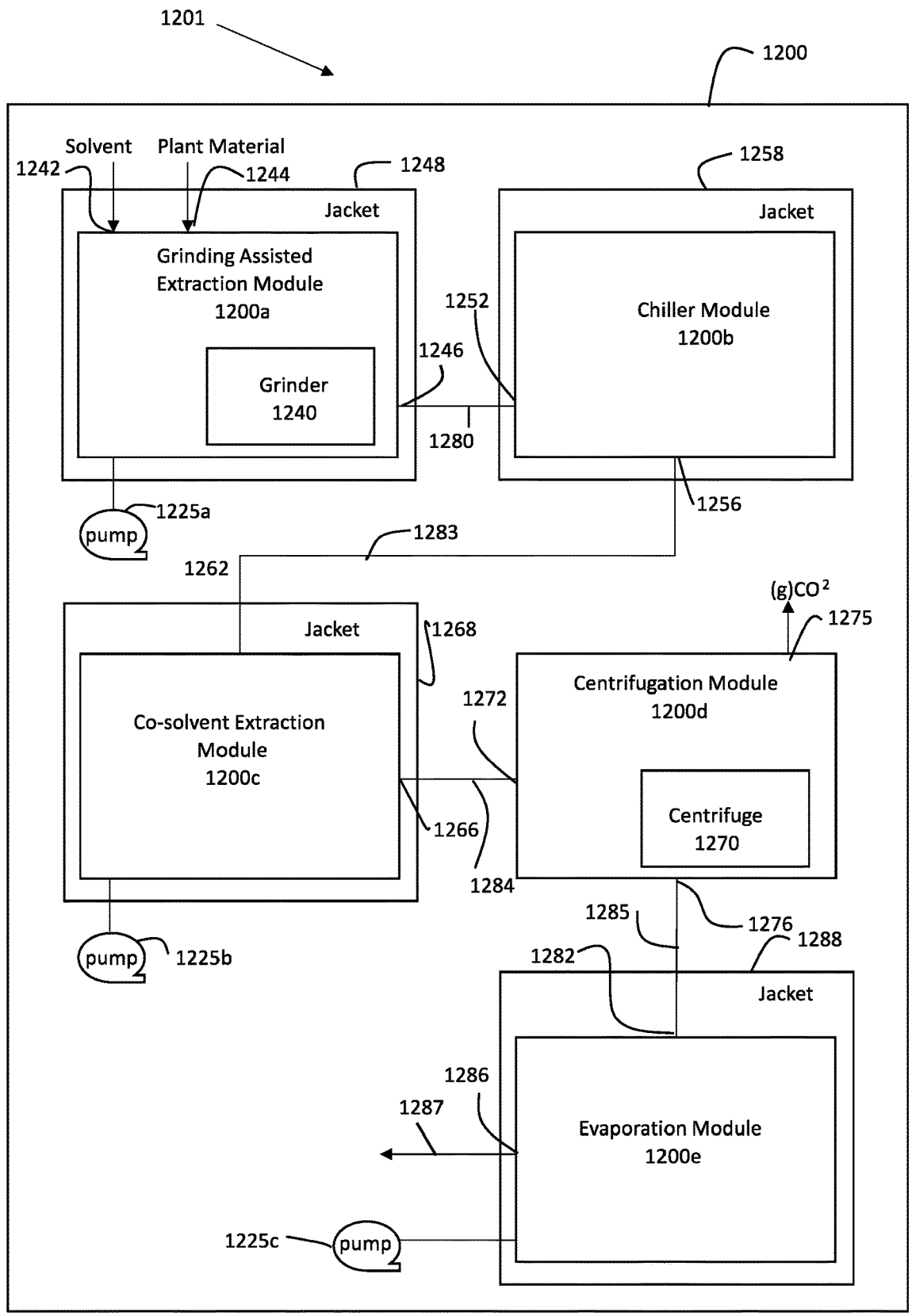
FIG. 15 is a schematic of an extraction unit according to various embodiments described herein.

FIG. 15 illustrates an extraction unit 1201 that may be used to perform extraction method 1100 or variation thereof according to various embodiments. Those skilled in the art will recognize, however, that extraction unit 1201 may also be utilized to perform other extraction methods. Similarly, extraction method 1100 may be performed utilizing other extraction unit apparatuses and configurations. In some embodiments, extraction unit 1201 is used in system 10 (FIGS. 1 & 2) instead of or in addition to extraction unit 201. In one example, extraction unit 201 comprises a vessel wherein heat is applied to cause complete or partial separation of solvent from extract via targeted evaporation and/or vaporization without sonication. In a further embodiment, extraction unit 1201 used separately or within system 10 may be subject to control as described with respect to FIGS. 12 & 13.

The extraction unit 1201 includes an extraction vessel 1200. The extraction vessel 1200 may comprise one or more interior volumes in which one or more extraction processes may be performed. In the illustrated embodiment, the extraction vessel 1200 is shown including various modules 1200a, 1200b, 1200c, 1200d, 1200e for performing particular extraction processes within a series of interior volumes or vessels of the extraction vessel 1200. It is to be appreciated that one, more, or all such extraction processes may be performed in a same interior volume.

The extraction unit 1201 may include various extraction components such as one or more grinders 1240, temperature modification components, pressure modification components, and/or centrifuges 1270. Grinders 1240 may be utilized to grind plant material within an interior volume of the extraction vessel 1200. Temperature modification components may be configured to control temperature within the one or more interior volumes of the extraction vessel 1200. For example, the extraction vessel 1200 may comprise one or more jackets 1248, 1258, 1268, 1288, which may be configured as described above and elsewhere herein. During operation, heating or cooling fluids may be flowed through the one or more jackets 1248, 1258, 1268, 1288 to maintain desired high and/or low temperatures within respective interior volumes. The thermal fluids may be supplied as described above with respect to FIG. 2 or elsewhere herein. As also described above, other temperature modification techniques may be used, such as heating elements or radiation energy. The extraction unit 1201 may include one or more pressure modification components configured to modify or maintain a pressure within an interior volume of the extraction vessel 1200. For example, pressure modification components may be operable to generate and/or maintain high or low-pressure environments within the one or more interior volumes of the extraction vessel 1200. In the illustrated embodiment, the extraction vessel 1200 fluidically couples to one or more pumps 1225a, 1225b, 1225c operable to generate above atmosphere or vacuum pressures within the one or more interior volumes of the extraction vessel 1200. The extraction unit 1201 may include one or more centrifuges 1270 to apply centrifugal force to extract process material. The extraction unit 1201 may also comprise various ports, e.g., plant material ports 1242; solvent ports 1244; extraction process feed ports 1252, 1262, 1272, 1282; discharge ports 1246, 1256, 1266, 1276, 1286; exhaust ports 1275, or co-solvent ports 1264. These ports may comprise separate ports or one or more ports may comprise a combined port. In some embodiments, one or more of a plant material port 1242; solvent port 1244; extraction process feed port 1252, 1262, 1272, 1282; discharge port 1246, 1256, 1266, 1276, 1286; exhaust ports 1275, or co-solvent ports 1264 may individually comprise multiple ports.

In the illustrated embodiment, the extraction vessel 1200 includes a grinding assisted extraction module 1200a, a chiller module 1200b, a co-solvent extraction module 1200c, a centrifugation module 1200d, and an evaporation module 1200e. While FIG. 15 illustrates five extraction modules 1200a, 1200b, 1200c, 1200d, 1200e in which discrete extraction processes may be performed in-line within subsections of the interior volume or a series of interior volumes of the extraction vessel 1200, as described in more detail below, it will be appreciated that the extraction vessel 1200 may include fewer or additional interior volumes in which such associated processes may be executed. For example, chilling may be accomplished in a same interior volume as grinding assisted extraction, co-solvent extraction may be executed in a same or different interior volume as chilling and/or centrifugation, or centrifugation may be executed in a same or different interior volume as grinding assisted extraction, co-solvent extraction, chilling, and/or evaporation. Additionally, the extraction vessel 1200 may include additional extraction vessels that perform parallel extraction processes or different extraction processes, such as multiple extraction processes selected from those described herein. In one embodiment, the extraction vessel 1200 does not include an evaporation module 1200*d*. In some embodiments, the extract obtained from such same or different extraction processes may be further processed as described herein, e.g., as described with respect to FIGS. 10 & 11 and/or fed into condenser 301 unit or winterization unit 400 of system 10 (see FIGS. 1 & 2), or according to known processes in the art.

As introduced above, the extraction vessel 1200 may include a grinding assisted extraction module 1200*a*. The grinding assisted extraction module 1200*a* may include a grinder 1240 comprising one or more grinding devices for grinding plant material. Grinder 1240 may be housed within an interior volume of the grinding assisted extraction module 1200*a*.

The grinding assisted extraction module 1200*a* may include a plant material port 1242 for receiving plant material into the interior volume, a solvent port 1244 for receiving solvent into the interior volume, and a discharge port 1246 for discharging extract process material.

The grinding assisted extraction module 1200*a* may include a temperature modification component for controlling temperature within the interior volume. In the illustrated embodiment, the temperature modification component comprises a jacket 1248 for receiving a cooling or heating fluid. Other temperature modification components may be used. For example, cooling or heating elements such as fluid lines may extend within the interior volume to heat or cool the extract process material.

The grinding assisted extraction module 1200*a* may include one or more a pressure modification components for modifying or maintaining a pressure within the interior volume. In the illustrated embodiment, the grinding assisted extraction module 1200*a* includes a pressure modification component comprising a pump 1225*a* in fluid communication with the interior volume of the grinding assisted extraction module 1200*a*. The pump 1225*a* is operable to increase or decrease pressure within the interior volume of the grinding assisted extraction module 1200*a*. It will be appreciated that in some embodiments, the grinding assisted extraction module 1200*a* does not include a temperature modification component, pressure modification component, or both.

The grinding assisted extraction module 1200*a* may include one or more grinders 1240. For example, the grinder 1240 may comprise a grinding/milling apparatus, such as an impingement, cutting, or impact type grinding/milling apparatus such as a roller mill, grinding mill, cutting mill, knife mill, hammer mill, jaw crusher, ball mill, jar mill, jet mill, disc mill, mortar grinder, gristmill, or pulverizer. In one embodiment, grinder 1240 may comprise a micronization grinder configured to generate micron scale pieces of plant material.

In an operation with respect to extraction method 1100, plant material and solvent may be supplied into the interior volume through the plant material port 1242 and solvent port 1244. Solvent and plant material may be supplied in a ratio of between approximately 2:1 and approximately 4:1 solvent to plant material on a weight basis. Higher solvent to plant material ratios may also be used, but may increase costs. The solvent may comprise a non-polar solvent, polar solvent, or both. In one embodiment, the solvent comprises a nonpolar solvent, such as glycerol monooleate. With the plant material in intimate contact with the solvent within the interior volume, the grinder 1240 may particulate the plant material to generate micron scale pieces of plant material. While larger average particle sizes may be used, the grinder 1240 may particulate the plant material to an average particle size of 100 microns or less. More preferably, the grinder 1240 may be configured to particulate the plant material to an average particle size of 40 microns or less. A fluid, such as a cooling fluid, may be flowed through the jacket 1248 to obtain a desired temperature during grinding assisted extraction. The process material within the grinding assisted extraction module 1200*a* during the grinding assisted extraction process may be maintained at approximately 80° C. or less, approximately 60° C. or less, approximately 50° C. or less, or more preferably approximately 40° C. or less, such as approximately 30° C. or less, or approximately 20° C. or less. Pump 1225*a* may be operated to provide a desired pressure within the interior volume. For example, when grinding assisted extraction in solvent 1102 includes low-pressure, pump 1225*a* may be operated to provide a desired vacuum pressure within the interior volume. For example, the interior volume of the grinding assisted extraction module 1200*a* may be held at a low vacuum (approximately 760 torr to approximately 25 torr), a medium vacuum (approximately 25 torr to approximately $10^{-3}$ torr), a high vacuum (approximately $10^{-3}$ to approximately $10^{-9}$ torr), an ultra high vacuum (approximately $10^{-9}$ to approximately $10^{-12}$ torr), an extremely high vacuum (positive pressure less than approximately $10^{-12}$ torr), or a perfect vacuum (0 torr). In some embodiments, grinding assisted extraction 1102 may be performed in 20 minutes or less, or between approximately 20 minutes and approximately 40 minutes, such as approximately 30 minutes.

Prior to extraction, the plant material may be preprocessed into pieces having a largest dimension of approximately 1 to approximately 2 inches or less as described above. The largest dimension may be taken as an average. Other size pieces may be used, such as larger pieces having a largest dimension less than 5 inches or less than 3 inches or smaller pieces having a largest dimension less than 1 inch or less than half an inch, for example. Larger pieces may also be used but may reduce yield and/or increase extraction time and overall process efficiency. In one embodiment, the plant material is preprocessed into pieces having average dimensions of between approximately 800 microns to approximately 1400 microns. In one embodiment, the extraction unit 1201 may include or be configured to operate in conjunction with a preprocessing subsystem comprising a preprocess grinding apparatus. The preprocessing subsystem may be in-line with the extraction vessel 1200 or a delivery system, as described in more detail elsewhere herein, to grind plants prior to the ground pieces for feeding into the extraction vessel 1200. For example, a mechanical cutter or grinder may preprocess plant material and the ground plant material may then be transported, which may be metered, as described above, into the extraction vessel 1200 via the delivery subsystem. In one embodiment, the delivery system includes an integrated preprocessing system comprising a preprocess grinder. In a further embodiment, plant material may be fed into the extraction vessel 1200 and therein be preprocessed using grinder 1240 or another grinder with or without intimate contact with solvent. Thus, grinder 1240 or another grinder may be used to cut plant material into smaller pieces as described herein and thereafter the plant material may be further ground while in intimate contact with solvent for grinding assisted extraction 1102, which may take place in a same or different interior volume.

The grinding assisted extraction module 1200a may include a discharge port 1246 for the discharge of the extract process material following extraction. A transport line 1280 may couple to the discharge port 1246 to provide a flow path for transport of discharged extract process material to the chiller module 1200b.

The chiller module 1200b may include an interior volume and a feed port 1252 through which to receive extract process material into the interior volume for chilling processing. A discharge port 1256 may be located for discharge of the chilled extract process material. The chiller module 1200b may include one or more temperature modification components for controlling temperature within the interior volume. In the illustrated embodiment, the chiller module 1200b includes a temperature modification component comprising a jacket 1258 for receiving a cooling fluid. Other temperature modification components may be used, such as those described above and elsewhere herein. As noted above, in some configurations, the chiller module 1200b may be integrated with one or more internal volumes or components of the extraction vessel 1200, such as the grinding assisted extraction module 1200a, co-solvent extraction module 1200c, or centrifugation module 1200d. For example, the chiller module 1200b may be incorporated with the grinding assisted extraction module 1200a wherein the temperature control apparatus, e.g., jacket 1248, may be supplied with a cooling fluid to chill the extract process material. A transport line 1283 may couple to the discharge port 1256 to provide a flow path for transport of extract process material between the chiller module 1200b and the co-solvent extraction module 1200c.

In an operation with respect to extraction method 1100, the homogeneous mixture generated from the grinding assisted extraction 1102 may be chilled in the chiller module 1200b prior to addition of liquid $CO_2$ co-solvent. The mixture is preferably cooled to approximately 30° C. or less, such as approximately 24° C. or less, such as between approximately 24° C. and approximately −18° C. When the co-solvent includes additional or other co-solvents, such additional or other co-solvents may be added prior, during, or after the cooling phase. In one embodiment, the mixture may be held at between approximately 21° C. and approximately 24° C. for a period of time before addition of the $CO_2$ co-solvent. It will be appreciated that some methodologies may skip the cooling process or may include addition of one or more co-solvents during the cooling process. Upon reaching a desired temperature, the cooled extract process material may be discharged from discharge port 1256 into transport line 1283.

The co-solvent extraction module 1200c may also include a feed port 1262 for receiving extract process material into its interior volume, a co-solvent port 1264 for receiving solvent into the interior volume, and a discharge port 1266 for discharging extract process material including co-solvent. The co-solvent extraction module 1200c may include one or more temperature modification components for controlling temperature within the interior volume. In the illustrated embodiment, the co-solvent extraction module 1200c includes a temperature modification component comprising a jacket 1268 for receiving a cooling or heating fluid. Other temperature modification components may be used, such as those described above and elsewhere herein. The co-solvent extraction module 1200c may include one or more pressure modification components for modifying or maintaining a pressure within the interior volume. In the illustrated embodiment, co-solvent extraction module 1200c includes or operatively associates with a pressure modification component comprising a pump 1225b in fluid communication with the interior volume to increase or decrease a pressure therein.

In an operation with respect to co-solvent extraction 1106 of extraction method 1100, liquid $CO_2$ may be added to the extract process material via the co-solvent port 1264 of the co-solvent extraction module 1200c. The liquid $CO_2$ may be provided at a ratio of approximately 4 parts liquid $CO_2$ to approximately 1 extract process material to approximately 1 part liquid $CO_2$ to approximately 2 parts extract process material. For example, liquid $CO_2$ may be added to the extract process material at a ratio of approximately 3:1 or more preferably approximately 1:1, on a weight basis. In some embodiments, higher or lower ratios may be used. The liquid $CO_2$ may be maintained in a subcritical liquid phase during co-solvent extraction 1106. For example, a cooling fluid may be flowed through the jacket 1268 to obtain a desired temperature during co-solvent extraction 1106. According to various embodiments, the co-solvent extraction module 1200c may maintain extract process material at approximately 30° C. or less, such as approximately 24° C. or less, between approximately 24° C. and approximately 21° C., or between approximately 24° C. and approximately −18° C. In one example, the extract process material may be maintained at approximately 21° C. or approximately 21° C. or less. Pump 1225b may also be operated to provide an above atmosphere pressure that corresponds with the process material temperature such that the combination of pressure and temperature maintains the $CO_2$ in a subcritical liquid phase. Beneficially, the pressure required to maintain the $CO_2$ in a subcritical liquid phase may be lower than that required for supercritical $CO_2$ techniques at similar temperatures. While higher pressures may be used, pressure may be less than approximately 72.79 atm (55,320 torr) or less than approximately 20 atm (15,200 torr) based on temperature combination. In some embodiments, co-solvent extraction 1106 may be performed in as few as approximately 20 minutes or less, such as approximately 10 minutes or less. In one example, co-solvent extraction 1106 may be performed for between approximately 20 minutes and approximately 10 minutes. While less efficient, longer co-solvent extraction times may be used in some instances.

As noted above, in some configurations, the co-solvent extraction module 1200c may be integrated with one or more of the grinding assisted extraction module 1200a, chiller module 1200b, centrifugation module 1200d, or evaporation module 1200e. For example, a grinder 240 and/or centrifuge 1270 may be positioned within the interior volume of the co-solvent extraction module 1200c.

A transport line 1284 may couple to the discharge port 1266 to provide a flow path for transport of extract process material including co-solvent from the co-solvent extraction module 1200c to the centrifugation module 1200d. In one embodiment, transport line 1284 may include a temperature modification component such as a jacket to receive a heated or cooled fluid or other device to modify or maintain a temperature of the extract process material. For example, the transport line 1284 may include a jacket to receive a heated fluid to heat the extract process material to greater than approximately 23° C., greater than approximately 25° C., greater than approximately 27° C., greater than approximately 29° C., or between approximately 23° C. and approximately 30° C., between approximately 24° C. and approximately 29° C., between approximately 24° C. and approximately 27° C., such as approximately 24° C., approximately 25° C., approximately 26° C., approximately 27° C., approximately 28° C., approximately 29° C., approximately 30° C., or approximately 31° C. prior to delivering the process material to the centrifugation module 1200d. In some embodiments, the centrifugation module 1200d includes a holding vessel comprising a temperature modification component in which the extract process material may be heated prior to centrifugation 1106.

The centrifugation module 1200d may include a feed port 1272 for receiving extract process material into its interior volume. An exhaust port 1275 may be provided for exhausting gas from the interior volume of the centrifugation module 1200d. A discharge port 1276 may be provided for discharging extract process material from the interior volume of the centrifugation module 1200d. One or more centrifuges 1270 may be provided within the interior volume for rotating the extract process material to apply centrifugal force to the material. Centrifugation may cause an increase in temperature that drives transition of liquid $CO_2$ co-solvent to gas, allowing the $CO_2$ gas to exit the extract process material. Thus, the pressure and temperature combination of the extract process material prior to centrifugation may be near liquid to gas phase transition such that a mild increase in temperature transition the liquid $CO_2$ to gas. The gas may discharge through exhaust port 1275. The $CO_2$ gas may be subsequently condensed for reuse. A pump may be in fluid communication with the exhaust port 1275 to generate a vacuum for pulling the gases through the exhaust port 1275. The centrifugation module 1200d may also include an expansion vessel (not shown) as described above with respect to the centrifugation 1106 step of extraction method 1100 wherein further degassing may take place. The expansion vessel may be passively or actively heated to accelerate degassing. The gas may be exhausted as described with respect to exhaust port 1275.

The centrifuge 1270 may be utilized to generate a three-phase separation that includes solid, oil, and water phases. In various embodiments, centrifuge speeds range from approximately 9,000 rpm and approximately 12,000 rpm. Greater or lower speeds may be used. Greater speeds may increase temperature to a greater extent. The centrifugation module 1200d may also include a solids discharge port (not shown) for removal of solids following centrifugation. The supernatant including the solvent/extract material may be discharged through the discharge port 1276 into transport line 1285. In some embodiments, the water phase and oil phase are separated and the water phase is subjected to evaporation or vaporization and controlled condensation to separate solvent and extract components, wherein the condensed extract components may be subsequently combined with the oil phase or otherwise collected for further purification or use.

Transport line 1285 may couple to additional processing apparatuses or storage vessels. In the illustrated embodiment, transport line 1285 couples to feed port 1282 of an evaporation module 1200e. In one embodiment, the evaporation module 1200e is optional. In some embodiments, the evaporation module 1200e is integrated with the centrifugation module 1200d. The extraction vessel 1200 also includes an evaporation module 1200e configured to convert all or a portion of the supernatant (solvent/extract mixture) to vapor for separation of all or a portion of the solvent. In some embodiments, the extraction vessel 1200 does not include an evaporation module 1200e. The evaporation module 1200e may be configured to convert all or a portion of the mixture to vapor in a relatively low temperature and low-pressure environment, e.g., as described above with respect to step 906 of FIG. 10 and extraction vessel 200 of FIGS. 1 & 2. Thus, the evaporation module 1200e may include a temperature modification component such as a jacket 1288 for receiving a heating fluid and be coupled to a pressure component such as a pump 1225c for creating a vacuum pressure environment within the evaporation module 1200e to convert all or a portion of the solvent/extract mixture to vapor. However, in some examples, the evaporation module 1200e may not include a transducer, agitator, or both.

In an operation, the extraction vessel 1200 described with respect to FIG. 15 may be utilized to perform the extraction method 1100 described with respect to FIG. 14 including grinding assisted extraction in solvent 1102, co-solvent extraction 1104 including subcritical liquid $CO_2$ extraction, and centrifugation 1106 as described above. The resulting solvent/extract mixture may be heated at a low temperature and subjected to a low-pressure environment in evaporation module 1200e as described above with respect to extraction vessel 200. By providing a vacuum pressure, vapor transition temperatures of the solvent/extract mixture components may be reduced to avoid degradation of extract components. Temperature may be increased, e.g., to temperatures above approximately 33° C. to aid in evaporation as vacuum gently pulls gas from the solvent/extract mixture. Vapor may be discharged through discharge port 1286 into transport line 1287. Transport line 1287 may carry generated vapor and couple to additional processing apparatuses or storage vessels. For example, transport line 1287 may couple to a condenser configured for controlled condensation, such as condenser unit 301 (see, e.g., FIGS. 1, 2, & 4), to separate all or a portion of the solvent from the extract to generate a crude extract. In some embodiments, only a portion of the supernatant is subject to evaporation and/or vaporization. In one example, a portion of the vapor including extract is condensed and separated from a portion of the vapor including solvent and the condensed extract is added to the remaining supernatant or a purified or isolated portion thereof. A discharge port and or transport line may be provided for remaining supernatant in the liquid phase for transport for further processing or reintroduction of condensed extract components.

Further distillation or purification may also be utilized to purify the crude extract, e.g., as described above with respect to system 10 (FIGS. 1-9) and/or relevant steps of methods 900, 918 (FIGS. 10 & 11). In some embodiments, further distillation and/or purification of the crude extract or solvent/extract mixture components may utilize other or different separation and/or purification apparatuses than described with respect to FIGS. 1-11. In some embodiments, further distillation or purification may result in ultra-purification. In some embodiments, purification of extract and/or solvent/extract mixture may include steam distillation, microwave assisted distillation, hydro-distillation, rotavaporator, open dish evaporation, supercritical $CO_2$, Enfleurage, Soxhlet, or combinations thereof.

Extraction vessel 1200 of FIG. 15 may be a standalone system suitable for supplying extracts, derivatives, or isolates thereof. In some embodiments, extraction vessel 1200 does not include on or more modules. For example, in one embodiment, extraction vessel 1200 does not include evaporation vessel 1200e.

In one embodiment, an extraction method includes grinding plant material in the presence of a polar or nonpolar solvent, performing subcritical liquid $CO_2$ extraction at low-pressure and low temperature, and then subjecting the extract process material to centrifugation, as described above with respect to extraction method 1100 and elsewhere herein. Heat, such as heat accompanying the centrifugation process, may drive phase transition of subcritical liquid $CO_2$ to gas, thereby removing all or a portion of the $CO_2$ co-solvent from the mixture. The supernatant may be collected and processed for removal of remaining solvent, such as by processing steps described herein. The method may be used to obtain a full spectrum extraction.

In one example, a solvent comprising a nonpolar solvent, such as Glycerol monooleate is added to an extraction vessel at approximately a 2:1 ratio by weight to plant material. The plant material is preferably in pieces of approximately 1 inch to approximately 2 inches or less. The solvent and plant material is mixed at approximately room temperature for approximately 15 minutes to achieve a uniform mixture. Grinding assisted extraction is then performed for approximately 15 minutes at a temperature reaching approximately 48° C. (120° F.) in a Hockmeyer immersion mill. The mixture is then brought to a temperature of approximately 21° C. (69° F.) and pressure of approximately 5.4 bar ($4.05 \times 10^3$ torr) and subcritical $CO_2$ is added and co-solvent extraction is performed for approximately 30 minutes. The chilling and co-solvent extraction step may be performed in a jacketed pressure vessel with a scraping blade mixer. The extract process material is then warmed to approximately 36° C. introduced into a centrifuge for separation into water, oil, solids and gasses.

In one example, the nonpolar solvent comprises a glycerol, e.g., glycerol monooleate ($C_{21}H_{40}O_4$). Glycerol monooleate is a clear amber or pale yellow liquid that is considered insoluble in water and oil soluble. During the extraction process, plant material may be micronized in the presence of glycerol monooleate. Particulate sizes may be as described above. As introduced above, the intimate grinding of plant material and glycerol monooleate drives cell-to-cell contact and solvent interaction. Glycerol monooleate may operate as a polarization component and absorption component that takes plant constituents into its bulk wherein glycerol monooleate molecularly interacts with oils to form molecular bonds with plant material to form a carrier liquid for plant constituents such as essential oils, cannabinoids, terpenes, and flavonoids.

In any of the above examples or another example, and with further reference to FIGS. 12 & 13, the extraction system 10 and/or extraction unit 1200 includes or is operatively integrates with a control system 1000 comprising a controller 1010 operable to control system operations 1015, e.g., processes and parameters. In one embodiment, the controller 1010 may be operable to control parameters such a temperature of product, processing materials, or environment with respect to one or more sub-process equipment, transport lines 14, 16, 18, 20, 22, 24, 26, 28, 30, 1280, 1283, 2084, 1285, 1287 or combinations thereof. For example, the controller 1010 may be operable to actuate valves to control flow or pressure, initiate or adjust operations of pumps, heaters, coolers, agitators, or other system operations 1015. Control system 1000 may be used to control operations of extraction unit 1201 alone or as part of extraction system 10 or unit thereof.

In various embodiments, the control system 1000 may include or communicate with one or more sensors 1020 to obtain extraction process data 1030 from which the controller 1010 analyzes to determine various control operations. The extraction process data 1030 may be transmitted from the one or more sensors 1020 to the controller 1010 via wired or wireless communication port. For example, the communication port, which may include multiple communication ports each associated with one or more sensors 1020 may include a transmitter or transceiver to transmit the extraction process data 1030 to communication port 1040, which may include or communicate with a receiver or transceiver to receive the transmitted extraction process data 1030. In some embodiments, the one or more sensors 1020 include thermal sensors, pressure sensors, optical sensors, video or image sensors, proximity sensors, flow sensors, proximity sensors, motion sensors, moisture sensors, weight sensors, sound or electromagnetic wave sensors (transmitter, receiver, or transceivers), capacitance sensors, or other sensors.

FIG. 12 provides an overview of the control system 1000 for controlling system operations 1015 as described herein. The control system 1000 comprises a flexible platform from which various tasks or functions related to the operations of the extraction system, e.g., controlling or monitoring the operations of the system.

The control system 1000 may include a controller 1010 configured to perform various monitoring and control tasks with respect to the extraction system. As introduced above, the controller 1010 may be configured to operatively associate with one or more sensors 1020 positioned to sense, detect, or measure conditions of the extraction system in real-time. The controller 1010 may be configured to route or make available operation data to one or more operation databases 1060 or user interfaces 1050. The operation database 1060, for example, may be accessed by the controller 1010 to retrieve, store, or archive control system data, which may include raw, processed, or analyzed operation data, events, as well as parameter definitions, including rules, statistics, tables, algorithms, or other data used to process or analyze data including generating or identifying operational conditions. Sensors 1020 may collect operation data comprising extraction process data and transmit, either wireless or by wired connection, the extraction process data to the controller 1010, as introduced above. The operations database 1050 may include files comprising instructions executable by the controller 1010 to perform one or more aspects of a control program. The controller 1010 a processing unit 1070 as shown in FIG. 13 for executing the instructions. The controller 1010 may execute the control program and be configured to interface the functionalities of the controller 1010 with users via one or more user interfaces 1050. The control program 120 may define various administrative parameters, e.g., definitions or settings, of the control system 1000 such as operational and administrative decision rules including set points, operational condition identification, and analysis parameters, any of which may include customizable definitions to fit a desired application. For example, the controller 1010 may be operatively associated with one or more processes of the extraction system to monitor, collect, analyze, process, and/or communicate data indicative of operational conditions, events, or states as defined by the control program. In various embodiments, the control program includes selectable processing protocols including set points definitions, threshold definitions, trigger event definitions, and/or response definitions.

The controller 1010 may also be configured to process the operation data. For example, the controller 1010 may analyze the operation data to determine operational conditions, format the operation data into a desired format or generate reports, e.g., enter select data or analyzed data into predefined forms or according to requests received from users interfaces 1050.

In various embodiments, the controller 1010 may be programmed to activate, deactivate, or modulate one or more system actuators 1115*a*, motors 1115*b*, pumps 1115*c*, valves 1115*d*, heaters 1115*e*, coolers 1115*f*, transducers 1115g, or combination thereof. The controller 1010 perform the above operations according to programed sequences according to a formula for example, upon receiving an instruction from a user interface 1050, or in response to extraction process data 1030 received from one or more sensors 1020. Sensors 1020 may include temperature sensors 1020a, pressure sensors 1020b, flow sensors 1020c, feed sensors 1020d, volume sensors 1020e, position sensors 1020f, as well as any other sensor, including those described elsewhere herein. As introduced above, sensors 1020 may transmit extraction process data 1030 via wired or wireless connection to the controller 1010. On or more sensors 1020, for example, may include a communication port 1020 configured to send electronic communication signals. For example, sensors 1020 may include a transmitter or transceiver for two-way communication with a communication port 1040 comprising a transceiver in communication with controller 1030. For example, the controller 1010 may initiate collection of extraction process data 1030 from a sensor. The controller 1010 may then activate, deactivation, or modulate a system operation 1115 based on the extraction process data 1030 collected by the sensor 1020 and transmitted to the controller 1010. The controller 1010 may analyze the extraction process data 1030 communicated from one or more of the sensors 1020 operatively associated with various sub-process equipment and compare the data to thresholds and parameters provided by a predefined program selected by user and then actively modulate system operations 1115 to conform the selected program.

As introduced above, the controller 1010 may be configured to communicate signals to one or more interfaces, e.g., programs, control system or external devices, user access devices or applications, or indicators which reflect a condition, event, state, activity, or function of the extraction system. For example, one such indicator may include a notification, which may include activation of a warning light, an audible alert, or a message sent to and displayed on a graphical display associated with a local or remote user interface such as a system control panel, computer, or personal electronic device, such as a smart phone.

Analysis of operation data may include the controller 103 utilizing administrative parameters comprising analysis tools to determine, calculate, or classify an operational condition, event, or state and then performing or initiating a predefined response or action in accordance with administrative decision rules specified in the control program. For example, the controller 1010 may compare raw or processed operation data or an operational condition determined using such data to predefined set points. Set points may include measurable standards identified or specified by a user or otherwise defined in the control program. Set points may include, for example, pressure or temperature in extraction vessel or short-path distillation unit, mechanical agitation rates, transducer frequency, transducer orientation, filter unit flow, preheater temperature, depth of solvent or biomass within the extraction vessel, valve states, filter efficiencies, expected remaining life of filters, or thermal medium temperature or flow rate.

When a set point comparison identifies an occurrence of a trigger event, the controller 1010 may respond in a predefined way. For example, the controller 1010 may transmit to one or more interfaces 1050 a notification, alert, or alarm. Additionally or alternatively the controller 1010 may perform or initiate a control operation specified by a decision rule, e.g., modulate an operation of the extraction system to address a trigger event. In various embodiments, set points or the predefined response to a trigger event may be statically or dynamically defined and, thus, may be beneficially configurable to adapt to different operational conditions or circumstances within any given application. In one embodiment, an authorized user may define the statically or dynamically defined response to one or more trigger events.

FIG. 13 illustrates various hardware units of a controller 1010 according to various embodiments. In general, the controller 1010 may include one or more processors, servers, databases, networks or network devices, and peripherals configured to obtain and transmit data and initiate control operations configured to perform in whole or in part the operations of the control program. As shown, the controller 1010 comprises a processing unit 1070, e.g., one or more electronic data processors or central processing units having logic control functionalities. The controller 1010 further comprises a memory unit 1075 comprising one or more electronic data storage mediums such as recording media, read-only, volatile, non-volatile, semi-conductor based, or other data storage mediums known in the art. The memory unit 1075, for example, includes one or more data storage mediums having stored thereon one or more programs or applications comprising software, firmware, or other instructions stored in one or more files executable by the processing unit 1070 to perform the various operations and functions of the controller 1010. The memory unit 1075 may further include database 1060. The instructions may include the control program 1080, which may include interaction with additional applications or services.

The controller 1010 may also include a communication unit 1090 configured to transmit and receive data. The communication unit 1090 may include one or more data ports, communication ports 1040, transmitters, receivers, transceivers, network cards, modems, gateways, routers, switches, firewalls, local, virtual, wide area, cloud/internet area, or internet-based distributed networks, Ethernet, wireless or wired digital communication devices, telecommunication devices, monitors, speakers, lights, buttons, knobs, or peripherals. The controller 1010 may also include or be operationally associated, e.g., via communication with associated communication ports coupled with sensors or system operations, with control and monitoring components such as sensors, actuators, valves, pumps, power switches, etc. for controlling or monitoring operational conditions of the extraction system.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth in this specification. Such embodiments may be obtained, for example, by combining, modifying, or reorganizing any of the disclosed steps, components, elements, features, aspects, characteristics, limitations, and the like, of the various non-limiting and non-exhaustive embodiments described in this specification. It will be appreciated various intermediate apparatuses and steps may be included without departing for the present disclosure.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an application of the described embodiments. Further, the use of a singular noun includes the plural, and the use of a plural noun includes the singular, unless the context of the usage requires otherwise. Additionally, the grammatical conjunctions "and" and "or" are used herein according to accepted usage. By way of example, "x and y" refers to "x" and "y". On the other hand, "x or y" refers to "x", "y", or both "x" and "y", whereas "either x or y" refers to exclusivity.

Any numerical range recited herein includes all values and ranges from the lower value to the upper value. For example, if a concentration range is stated as 1% to 50%, it is intended that values such as 2% to 40%, 10% to 30%, 1% to 3%, or 2%, 25%, 39% and the like, are expressly enumerated in this specification. These are only examples of what is specifically intended, and all possible combinations of numerical values and ranges between and including the lowest value and the highest value enumerated are to be considered to be expressly stated in this application. Numbers modified by the term "approximately" are intended to include +/−10% of the number modified.

The present disclosure may be embodied in other forms without departing from the spirit or essential attributes thereof and, accordingly, reference should be had to the following claims rather than the foregoing specification as indicating the scope of the invention. Further, the illustrations of arrangements described herein are intended to provide a general understanding of the various embodiments, and they are not intended to serve as a complete description. Many other arrangements will be apparent to those of skill in the art upon reviewing the above description. Other arrangements may be utilized and derived therefrom, such that logical substitutions and changes may be made without departing from the scope of this disclosure.

What is claimed is:

1. A cannabis oil extraction method, the method comprising:
    performing grinding assisted extraction comprising:
        grinding plant material in the presence of solvent to generate an extract process material mixture;
    performing co-solvent extraction using subcritical $CO_2$ comprising:
        adding liquid $CO_2$ to the extract process material mixture, and maintaining the extract process material mixture at a temperature and pressure combination sufficient to maintain the liquid $CO_2$ in a subcritical state;
    degassing the $CO_2$; and
    separating the extract process material mixture by centrifugation.

2. The method of claim 1, wherein the plant material ground in the presence of the solvent is wet plant material.

3. The method of claim 1, wherein a ratio of solvent to plant material present during the grinding assisted extraction is greater than 1:1 on a weight basis.

4. The method of claim 1, wherein a ratio of solvent to plant material present during the grinding assisted extraction is greater than 2:1 on a weight basis.

5. The method of claim 1, wherein grinding the plant material in the presence of solvent comprises grinding the plant material to micron scale.

6. The method of claim 5, wherein the plant material is ground to less than 20 microns during grinding assisted extraction.

7. The method of claim 1, wherein the solvent is a food grade solvent.

8. The method of claim 1, wherein the solvent is a non-polar solvent.

9. The method of claim 8, wherein the non-polar solvent is selected from pentane, hexane, benzene, toluene, carbon tetrachloride, benzene, glycerol monooleate, diethyl ether, hexane, methylene chloride, carbon dioxide, methane, ethylene, D-limonene, olive oil, soybean oil, coconut oil, medium chain triglycerides, methanol, ethanol, propylene glycol, polysorbates 20 and 80 (tween 20 and 80), poloxamer 188, chloroform, diethyl ether, deuterated chloroform, or combination thereof.

10. The method of claim 1, wherein the solvent is glycerol monooleate.

11. The method of claim 1, wherein the liquid $CO_2$ is added to the extract process material mixture at ratio of greater than approximately 1:1 co-solvent to mixture on a weight basis.

12. The method of claim 1, wherein the extract process material mixture is at a temperature between 30° C. and −18° C. and a pressure of between approximately 5.2 bar and approximately 72 bar when the liquid $CO_2$ is added to the mixture.

13. The method of claim 1, further comprising agitating the extract process material mixture during co-solvent extraction with the liquid $CO_2$.

14. The method of claim 1, wherein centrifugation separates the extract process material mixture into a solid phase, oil phase, and water phase.

15. The method of claim 14, wherein the oil phase comprises extract extracted from the plant material, and wherein the method further comprises:
    winterizing the extract in an inline winterization unit;
    filtering the winterized extract with a micron filter;
    preheating the filtered extract with a preheater;
    evaporating a first portion of the extract in an evaporation chamber of a short-path distillation unit, wherein a second portion of the extract passes through the evaporation chamber without evaporating;
    condensing the first portion of the extract in a vertical condenser; and
    evaporating one or more additional portions of the second portion of the extract in the same or one or more additional evaporation chambers at higher temperatures and condensing these one or more portions separately in the same or one or more additional vertical condensers to obtain refined cannabis oil pay product comprising cannabinoids isolated by weight.

16. The method of claim 1, wherein degassing the $CO_2$ comprises heating the extract process material mixture before or during centrifugation.

17. The method of claim 1, wherein at least a portion of the $CO_2$ is degassed during centrifugation.

18. The method of claim 1, wherein degassing the $CO_2$ comprises allowing a supernatant component of the separated extract process material mixture generated by the centrifugation to expand.

19. The method of claim 1, further comprising heating the extract process material mixture after the co-solvent extraction to drive degassing of the liquid $CO_2$ co-solvent.

20. The method of claim 19, wherein heating the extract process material mixture after the co-solvent extraction comprises heating the mixture to between 26° C. and 32° C.

21. The method of claim 1, wherein the solvent comprises a polar solvent and a non-polar solvent.

\* \* \* \* \*